United States Patent [19]

Theofan et al.

[11] Patent Number: 5,643,570
[45] Date of Patent: Jul. 1, 1997

[54] BPI-IMMUNOGLOBULIN FUSION PROTEINS

[75] Inventors: Georgia Theofan, Torrance, Calif.; Lynn S. Grinna, Middleburg, Va.; Arnold Horwitz, Los Angeles, Calif.

[73] Assignee: XOMA Corporation, Berkeley, Calif.

[21] Appl. No.: 64,693

[22] Filed: May 19, 1993

Related U.S. Application Data

[63] Continuation-in-part of Ser. No. 885,911, May 19, 1992, abandoned.

[51] Int. Cl.$^6$ .......................... C12N 15/12; C12N 15/00; A61K 39/395; C07K 19/00
[52] U.S. Cl. .................... 424/134.1; 435/252.3; 435/172.3; 435/320.1; 435/69.1; 530/387.3; 536/23.4
[58] Field of Search ................ 530/387.3; 435/240.2, 435/252.3, 69.1, 172.3, 320.1; 424/85.8, 134.1

[56] References Cited

U.S. PATENT DOCUMENTS

| | | |
|---|---|---|
| 4,816,567 | 3/1989 | Cabilly et al. . |
| 5,098,833 | 3/1992 | Lasky et al. .......................... 435/69.1 |
| 5,420,019 | 5/1995 | Theofan ................................ 435/69.1 |

FOREIGN PATENT DOCUMENTS

| | | |
|---|---|---|
| 8901486 | 2/1989 | WIPO . |
| 88/03414 | 4/1989 | WIPO . |
| 91/05758 | 3/1992 | WIPO . |
| 92/01370 | 9/1992 | WIPO . |
| 92/08298 | 4/1993 | WIPO . |

OTHER PUBLICATIONS

Lasky et al., J. Cell. Biol., 1990, 110:2221.
Harris et al., Tibtech, 1993, 11:42.
Osband et al., Immunol. Today, 1990, 11:193.
Cross et al., Infect. Immun., 1993, 61:2741.
Rhein, Biotechnology Newswatch, Oct. 4, 1993.
Natanson et al., Ann. Int. Med., 1994 120(9) 771–783.
Ashkenazi, et al., Proc. Natl. Acad. Sci. USA, "Protection against endotoxic shock by a tumor necrosis factor receptor immunoadhesin," 1991, vol. 88, pp. 10535–10539.
Aruffo, et al., Cell, "CD44 is the Principal Cell Surface Receptor for Hyaluronate," Jun. 29, 1990, vol. 61, pp. 1303–1313.
Bismuth, et al., Molecular Immunology, "A Human TCR–Ig Chimeric Protein Used to Generate a TCR α Chain Variable Region–Specific mAb," 1990, vol. 27, No. 11 pp. 1127–1136.
Capon, et al., Nature, "Designing CD4 immunoadhesins for AIDS therapy," Feb. 9, 1989, vol. 337, pp. 525–530.
Elsbach, et al., The Journal of Biological Chemistry, "Separation and Purification of a Potent Bactericidal/Permeability–increasing Protein and a Closely Associated Phospholipase A$_2$ from Rabbit Polymorphonuclear Leukocytes," Nov. 10, 1979, vol. 254, No. 21, pp. 11000–11009.

Gascoigne, et al., Proc. Natl. Acad. Sci. USA, "Secretion of a chimeric T–cell receptor–immunoglobulin protein," May 1987, vol. 84 pp. 2936–2940.
Goverman, et al., Cell, "Chimeric Immunoglobulin–T Cell Receptor Proteins Form Functional Receptors: Implications for T Cell Receptor Complex Formation and Activation," Mar. 23, 1990, vol. 60, pp. 929–939.
Gray, et al., The Journal of Biological Chemistry, "Cloning of the cDNA of a Human Neutrophil Bactericidal Protein," Jun. 5, 1989, vol. 264, No. 16, pp. 9505–9509.
Gregoire, et al., Proc. Natl. Acad. Sci. USA, "Engineered secreted T–cell receptor αβ heterodimers," Sep. 1991, vol. 88, pp. 8077–8081.
Harris, et al., J. Biochem, "Structural characterization of a recombinant CD4–IgG hybrid molecule," 1990, vol. 194, pp. 611–620.
Mariuzza, et al., The Journal of Biological Chemistry, "Secretion of a Homodimeric $V_\alpha C_k$ T–cell Receptor–Immunoglobulin Chimeric Protein," 1989, vol. 264, No. 13, pp. 7310–7316.
Ooi, et al., J. Exp. Med., "Endotoxin–neutralizing Properties of the 25kD N–Terminal Fragment and a Newly Isolated 30 kD C–Terminal Fragment of the 55–60 kD Bactericidal/Permeability–increasing Protein of Human Neutrophils," Sep. 1991, vol. 174, pp. 649–655.
Ooi, et al., The Journal of Biological Chemistry, "A 25–kDa NH$_2$–terminal Fragment Carries All the Antibacterial Activities of the Human Neutrophil 60–kDa Bactericidal/Permeability–increasing Protein," Nov. 5, 1987, vol. 262, No. 31, pp. 14891–14894.
Robinson, et al., Hum. Antibod. Hybridomas, "Chimeric mouse–human anti–carcinoma antibodies that mediate different anti–tumor cell biological activities," Apr. 1991, vol. 2, pp. 84–93.
Simon, et al., Proc. N.A.S., "Inhibition of RNA Synthesis in Escherichia coli by Levorphanol," 1964, vol. 51, pp. 877–883.
Simonsen, et al. Proc. Natl. Acad. Sci. USA, "Isolation and expression of an altered mouse dihydrofolate reductase cDNA," May 1983, vol. 80 pp. 2495–2499.
Stites, et al., Basic and Clinical Immunology, 1987, p. 32.
Weiss, et al., Blood, "Cellular and Subcellular Localization of the Bactericidal/Permeability–Increasing Protein of Neutrophils," Feb. 1987, vol. 69, No. 2, pp. 652–659.

(List continued on next page.)

Primary Examiner—Frank C. Eisenschenk
Attorney, Agent, or Firm—Marshall, O'Toole, Gerstein, Murray & Borun

[57] ABSTRACT

Disclosed are novel hybrid fusion proteins comprising at their amino terminus, bactericidal/permeability-increasing protein or a biologically active fragment thereof and, at their carboxy terminus, at least one immunoglobulin heavy chain constant domain useful in treating bacterial infection. Also disclosed are DNA sequences encoding such proteins, recombinant methods for production of the proteins, and pharmaceutical preparations containing the recombinant products.

28 Claims, 10 Drawing Sheets

OTHER PUBLICATIONS

Wigler, et al., *Cell*, "Transfer of Purified Herpes Virus Thymidine Kinase Gene to Culture Mouse Cells," May 1977, vol. 11, pp. 223–232.

Waldmann, et al., *Science*, "Monoclonal Antibodies in Diagnosis and Therapy," Jun. 1991, vol. 252, pp. 1657–1662.

Winter, et al., *Nature*, "Man–made antibodies," Jan. 24, 1991, vol. 349, pp. 293–299.

Weiss, et al., *Infection and Immunity*, "Environmental Modulation of Lipopolysaccharide Chain Length Alters the Sensitivity of *Escherichia coli* to the Neutrophil Bactericidal/Permeability–Increasing Protein," Feb. 1986, vol. 51, No. 2, pp. 594–599.

Marra, et al., *The Journal of Immunology*, "Bactericidal/Permeability–Increasing Protein Has Endotoxin–Neutralizing Activity," Jan. 15, 1990, vol. 144, No. 2, pp. 662–666.

Mannion, et al., *The Journal of Immunology*, "Preferential Binding of the Neutrophil Cytoplasmic Granule–Derived Bactericidal/Permeability Increasing Protein to Target Bacteria," Apr. 15, 1989, vol. 142, No. 8, pp. 2807–2812.

Tobias, et al., *The Journal of Biological Chemistry*, "A Family of Lipopolysaccharide Binding Proteins Involved in Responses to Gram–negative Sepsis," Sep. 25, 1988, vol. 263, No. 27, pp. 13479–13481.

Traunecker, et al., *Nature*, "Soluble CD4 molecules neutralize human immunodeficiency virus type 1," Jan. 7, 1988, vol. 331, pp. 84–86.

Linsley, et al., *J. Exp. Med.*, "Binding of the B Cell Activation Antigen B7 to CD28 Costimulates T Cell Proliferation and Interleukin 2 mRNA Accumulation," Mar. 1991, vol. 173, pp. 721–730.

Watson, Nature, 1991, 349:164.

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 31..1491

( i x ) FEATURE:
        ( A ) NAME/KEY: mat_peptide
        ( B ) LOCATION: 124..1491

( x i ) SEQUENCE DESCRIPTION: SEQ ID NO:1:

```
CAGGCCTTGA GGTTTTGGCA GCTCTGGAGG ATG AGA GAG AAC ATG GCC AGG GGC    54
                                 Met Arg Glu Asn Met Ala Arg Gly
                                 -31 -30                      -25
```

| | | | | | | | | | | | | | | | | |
|---|---|---|---|---|---|---|---|---|---|---|---|---|---|---|---|---|
| CCT | TGC | AAC | GCG | CCG | AGA | TGG | GTG | TCC | CTG | ATG | GTG | CTC | GTC | GCC | ATA | 102 |
| Pro | Cys | Asn | Ala | Pro | Arg | Trp | Val | Ser | Leu | Met | Val | Leu | Val | Ala | Ile | |
| | | | -20 | | | | -15 | | | | | -10 | | | | |
| GGC | ACC | GCC | GTG | ACA | GCG | GCC | GTC | AAC | CCT | GGC | GTG | GTG | GTC | AGG | ATC | 150 |
| Gly | Thr | Ala | Val | Thr | Ala | Ala | Val | Asn | Pro | Gly | Val | Val | Val | Arg | Ile | |
| | | -5 | | | | | 1 | | | | 5 | | | | | |
| TCC | CAG | AAG | GGC | CTG | GAC | TAC | GCC | AGC | CAG | CAG | GGG | ACG | GCC | GCT | CTG | 198 |
| Ser | Gln | Lys | Gly | Leu | Asp | Tyr | Ala | Ser | Gln | Gln | Gly | Thr | Ala | Ala | Leu | |
| 10 | | | | | 15 | | | | 20 | | | | | | 25 | |
| CAG | AAG | GAG | CTG | AAG | AGG | ATC | AAG | ATT | CCT | GAC | TAC | TCA | GAC | AGC | TTT | 246 |
| Gln | Lys | Glu | Leu | Lys | Arg | Ile | Lys | Ile | Pro | Asp | Tyr | Ser | Asp | Ser | Phe | |
| | | | | 30 | | | | | 35 | | | | | 40 | | |
| AAG | ATC | AAG | CAT | CTT | GGG | AAG | GGG | CAT | TAT | AGC | TTC | TAC | AGC | ATG | GAC | 294 |
| Lys | Ile | Lys | His | Leu | Gly | Lys | Gly | His | Tyr | Ser | Phe | Tyr | Ser | Met | Asp | |
| | | | 45 | | | | | 50 | | | | | 55 | | | |
| ATC | CGT | GAA | TTC | CAG | CTT | CCC | AGT | TCC | CAG | ATA | AGC | ATG | GTG | CCC | AAT | 342 |
| Ile | Arg | Glu | Phe | Gln | Leu | Pro | Ser | Ser | Gln | Ile | Ser | Met | Val | Pro | Asn | |
| | | 60 | | | | | 65 | | | | | 70 | | | | |
| GTG | GGC | CTT | AAG | TTC | TCC | ATC | AGC | AAC | GCC | AAT | ATC | AAG | ATC | AGC | GGG | 390 |
| Val | Gly | Leu | Lys | Phe | Ser | Ile | Ser | Asn | Ala | Asn | Ile | Lys | Ile | Ser | Gly | |
| | | 75 | | | | | 80 | | | | | 85 | | | | |
| AAA | TGG | AAG | GCA | CAA | AAG | AGA | TTC | TTA | AAA | ATG | AGC | GGC | AAT | TTT | GAC | 438 |
| Lys | Trp | Lys | Ala | Gln | Lys | Arg | Phe | Leu | Lys | Met | Ser | Gly | Asn | Phe | Asp | |
| 90 | | | | | 95 | | | | | 100 | | | | | 105 | |
| CTG | AGC | ATA | GAA | GGC | ATG | TCC | ATT | TCG | GCT | GAT | CTG | AAG | CTG | GGC | AGT | 486 |
| Leu | Ser | Ile | Glu | Gly | Met | Ser | Ile | Ser | Ala | Asp | Leu | Lys | Leu | Gly | Ser | |
| | | | | 110 | | | | | 115 | | | | | 120 | | |
| AAC | CCC | ACG | TCA | GGC | AAG | CCC | ACC | ATC | ACC | TGC | TCC | AGC | TGC | AGC | AGC | 534 |
| Asn | Pro | Thr | Ser | Gly | Lys | Pro | Thr | Ile | Thr | Cys | Ser | Ser | Cys | Ser | Ser | |
| | | | 125 | | | | | 130 | | | | | 135 | | | |
| CAC | ATC | AAC | AGT | GTC | CAC | GTG | CAC | ATC | TCA | AAG | AGC | AAA | GTC | GGG | TGG | 582 |
| His | Ile | Asn | Ser | Val | His | Val | His | Ile | Ser | Lys | Ser | Lys | Val | Gly | Trp | |
| | | 140 | | | | | 145 | | | | | 150 | | | | |
| CTG | ATC | CAA | CTC | TTC | CAC | AAA | AAA | ATT | GAG | TCT | GCG | CTT | CGA | AAC | AAG | 630 |
| Leu | Ile | Gln | Leu | Phe | His | Lys | Lys | Ile | Glu | Ser | Ala | Leu | Arg | Asn | Lys | |
| | 155 | | | | | 160 | | | | | 165 | | | | | |
| ATG | AAC | AGC | CAG | GTC | TGC | GAG | AAA | GTG | ACC | AAT | TCT | GTA | TCC | TCC | AAG | 678 |
| Met | Asn | Ser | Gln | Val | Cys | Glu | Lys | Val | Thr | Asn | Ser | Val | Ser | Ser | Lys | |
| 170 | | | | | 175 | | | | | 180 | | | | | 185 | |
| CTG | CAA | CCT | TAT | TTC | CAG | ACT | CTG | CCA | GTA | ATG | ACC | AAA | ATA | GAT | TCT | 726 |
| Leu | Gln | Pro | Tyr | Phe | Gln | Thr | Leu | Pro | Val | Met | Thr | Lys | Ile | Asp | Ser | |
| | | | | 190 | | | | | 195 | | | | | 200 | | |
| GTG | GCT | GGA | ATC | AAC | TAT | GGT | CTG | GTG | GCA | CCT | CCA | GCA | ACC | ACG | GCT | 774 |
| Val | Ala | Gly | Ile | Asn | Tyr | Gly | Leu | Val | Ala | Pro | Pro | Ala | Thr | Thr | Ala | |
| | | | 205 | | | | | 210 | | | | | 215 | | | |
| GAG | ACC | CTG | GAT | GTA | CAG | ATG | AAG | GGG | GAG | TTT | TAC | AGT | GAG | AAC | CAC | 822 |
| Glu | Thr | Leu | Asp | Val | Gln | Met | Lys | Gly | Glu | Phe | Tyr | Ser | Glu | Asn | His | |
| | | 220 | | | | | 225 | | | | | 230 | | | | |
| CAC | AAT | CCA | CCT | CCC | TTT | GCT | CCA | CCA | GTG | ATG | GAG | TTT | CCC | GCT | GCC | 870 |
| His | Asn | Pro | Pro | Pro | Phe | Ala | Pro | Pro | Val | Met | Glu | Phe | Pro | Ala | Ala | |
| | 235 | | | | | 240 | | | | | 245 | | | | | |
| CAT | GAC | CGC | ATG | GTA | TAC | CTG | GGC | CTC | TCA | GAC | TAC | TTC | TTC | AAC | ACA | 918 |
| His | Asp | Arg | Met | Val | Tyr | Leu | Gly | Leu | Ser | Asp | Tyr | Phe | Phe | Asn | Thr | |
| 250 | | | | | 255 | | | | | 260 | | | | | 265 | |
| GCC | GGG | CTT | GTA | TAC | CAA | GAG | GCT | GGG | GTC | TTG | AAG | ATG | ACC | CTT | AGA | 966 |
| Ala | Gly | Leu | Val | Tyr | Gln | Glu | Ala | Gly | Val | Leu | Lys | Met | Thr | Leu | Arg | |
| | | | | 270 | | | | | 275 | | | | | 280 | | |
| GAT | GAC | ATG | ATT | CCA | AAG | GAG | TCC | AAA | TTT | CGA | CTG | ACA | ACC | AAG | TTC | 1014 |
| Asp | Asp | Met | Ile | Pro | Lys | Glu | Ser | Lys | Phe | Arg | Leu | Thr | Thr | Lys | Phe | |
| | | | 285 | | | | | 290 | | | | | 295 | | | |

-continued

| | | | | | | | | | | | | | | | | |
|---|---|---|---|---|---|---|---|---|---|---|---|---|---|---|---|---|
| TTT | GGA | ACC | TTC | CTA | CCT | GAG | GTG | GCC | AAG | AAG | TTT | CCC | AAC | ATG | AAG | 1062 |
| Phe | Gly | Thr 300 | Phe | Leu | Pro | Glu | Val 305 | Ala | Lys | Lys | Phe | Pro 310 | Asn | Met | Lys | |
| ATA | CAG | ATC | CAT | GTC | TCA | GCC | TCC | ACC | CCG | CCA | CAC | CTG | TCT | GTG | CAG | 1110 |
| Ile | Gln 315 | Ile | His | Val | Ser | Ala 320 | Ser | Thr | Pro | Pro | His 325 | Leu | Ser | Val | Gln | |
| CCC | ACC | GGC | CTT | ACC | TTC | TAC | CCT | GCC | GTG | GAT | GTC | CAG | GCC | TTT | GCC | 1158 |
| Pro 330 | Thr | Gly | Leu | Thr | Phe 335 | Tyr | Pro | Ala | Val | Asp 340 | Val | Gln | Ala | Phe | Ala 345 | |
| GTC | CTC | CCC | AAC | TCC | TCC | CTG | GCT | TCC | CTC | TTC | CTG | ATT | GGC | ATG | CAC | 1206 |
| Val | Leu | Pro | Asn | Ser 350 | Ser | Leu | Ala | Ser | Leu 355 | Phe | Leu | Ile | Gly | Met 360 | His | |
| ACA | ACT | GGT | TCC | ATG | GAG | GTC | AGC | GCC | GAG | TCC | AAC | AGG | CTT | GTT | GGA | 1254 |
| Thr | Thr | Gly | Ser 365 | Met | Glu | Val | Ser | Ala 370 | Glu | Ser | Asn | Arg | Leu 375 | Val | Gly | |
| GAG | CTC | AAG | CTG | GAT | AGG | CTG | CTC | CTG | GAA | CTG | AAG | CAC | TCA | AAT | ATT | 1302 |
| Glu | Leu | Lys 380 | Leu | Asp | Arg | Leu | Leu 385 | Leu | Glu | Leu | Lys | His 390 | Ser | Asn | Ile | |
| GGC | CCC | TTC | CCG | GTT | GAA | TTG | CTG | CAG | GAT | ATC | ATG | AAC | TAC | ATT | GTA | 1350 |
| Gly | Pro 395 | Phe | Pro | Val | Glu | Leu 400 | Leu | Gln | Asp | Ile | Met 405 | Asn | Tyr | Ile | Val | |
| CCC | ATT | CTT | GTG | CTG | CCC | AGG | GTT | AAC | GAG | AAA | CTA | CAG | AAA | GGC | TTC | 1398 |
| Pro 410 | Ile | Leu | Val | Leu | Pro 415 | Arg | Val | Asn | Glu | Lys 420 | Leu | Gln | Lys | Gly | Phe 425 | |
| CCT | CTC | CCG | ACG | CCG | GCC | AGA | GTC | CAG | CTC | TAC | AAC | GTA | GTG | CTT | CAG | 1446 |
| Pro | Leu | Pro | Thr | Pro 430 | Ala | Arg | Val | Gln | Leu 435 | Tyr | Asn | Val | Val | Leu 440 | Gln | |
| CCT | CAC | CAG | AAC | TTC | CTG | CTG | TTC | GGT | GCA | GAC | GTT | GTC | TAT | AAA | | 1491 |
| Pro | His | Gln | Asn 445 | Phe | Leu | Leu | Phe | Gly 450 | Ala | Asp | Val | Val | Tyr 455 | Lys | | |

```
TGAAGGCACC  AGGGGTGCCG  GGGGCTGTCA  GCCGCACCTG  TTCCTGATGG  GCTGTGGGGC  1551
ACCGGCTGCC  TTTCCCCAGG  GAATCCTCTC  CAGATCTTAA  CCAAGAGCCC  CTTGCAAACT  1611
TCTTCGACTC  AGATTCAGAA  ATGATCTAAA  CACGAGGAAA  CATTATTCAT  TGGAAAAGTG  1671
CATGGTGTGT  ATTTTAGGGA  TTATGAGCTT  CTTTCAAGGG  CTAAGGCTGC  AGAGATATTT  1731
CCTCCAGGAA  TCGTGTTTCA  ATTGTAACCA  AGAAATTTCC  ATTTGTGCTT  CATGAAAAAA  1791
AACTTCTGGT  TTTTTTCATG  TG                                              1813
```

( 2 ) INFORMATION FOR SEQ ID NO:2:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met -31 | Arg -30 | Glu | Asn | Met | Ala | Arg -25 | Gly | Pro | Cys | Asn | Ala -20 | Pro | Arg | Trp | Val |
| Ser -15 | Leu | Met | Val | Leu | Val -10 | Ala | Ile | Gly | Thr | Ala -5 | Val | Thr | Ala | Ala | Val 1 |
| Asn | Pro | Gly | Val | Val 5 | Val | Arg | Ile | Ser | Gln 10 | Lys | Gly | Leu | Asp | Tyr 15 | Ala |
| Ser | Gln | Gln 20 | Gly | Thr | Ala | Ala | Leu 25 | Gln | Lys | Glu | Leu | Lys 30 | Arg | Ile | Lys |
| Ile | Pro | Asp 35 | Tyr | Ser | Asp | Ser | Phe 40 | Lys | Ile | Lys | His 45 | Leu | Gly | Lys | Gly |
| His | Tyr | Ser | Phe | Tyr | Ser | Met | Asp | Ile | Arg | Glu | Phe | Gln | Leu | Pro | Ser |

```
                50                          55                          60                          65
Ser  Gln  Ile  Ser  Met  Val  Pro  Asn  Val  Gly  Leu  Lys  Phe  Ser  Ile  Ser
                    70                       75                            80
Asn  Ala  Asn  Ile  Lys  Ile  Ser  Gly  Lys  Trp  Lys  Ala  Gln  Lys  Arg  Phe
                85                       90                       95
Leu  Lys  Met  Ser  Gly  Asn  Phe  Asp  Leu  Ser  Ile  Glu  Gly  Met  Ser  Ile
              100                      105                      110
Ser  Ala  Asp  Leu  Lys  Leu  Gly  Ser  Asn  Pro  Thr  Ser  Gly  Lys  Pro  Thr
         115                      120                      125
Ile  Thr  Cys  Ser  Ser  Cys  Ser  Ser  His  Ile  Asn  Ser  Val  His  Val  His
130                      135                      140                           145
Ile  Ser  Lys  Ser  Lys  Val  Gly  Trp  Leu  Ile  Gln  Leu  Phe  His  Lys  Lys
                   150                      155                           160
Ile  Glu  Ser  Ala  Leu  Arg  Asn  Lys  Met  Asn  Ser  Gln  Val  Cys  Glu  Lys
              165                      170                      175
Val  Thr  Asn  Ser  Val  Ser  Ser  Lys  Leu  Gln  Pro  Tyr  Phe  Gln  Thr  Leu
         180                      185                      190
Pro  Val  Met  Thr  Lys  Ile  Asp  Ser  Val  Ala  Gly  Ile  Asn  Tyr  Gly  Leu
         195                      200                      205
Val  Ala  Pro  Pro  Ala  Thr  Thr  Ala  Glu  Thr  Leu  Asp  Val  Gln  Met  Lys
210                      215                      220                           225
Gly  Glu  Phe  Tyr  Ser  Glu  Asn  His  His  Asn  Pro  Pro  Phe  Ala  Pro
                   230                      235                      240
Pro  Val  Met  Glu  Phe  Pro  Ala  Ala  His  Asp  Arg  Met  Val  Tyr  Leu  Gly
              245                      250                      255
Leu  Ser  Asp  Tyr  Phe  Phe  Asn  Thr  Ala  Gly  Leu  Val  Tyr  Gln  Glu  Ala
         260                      265                      270
Gly  Val  Leu  Lys  Met  Thr  Leu  Arg  Asp  Asp  Met  Ile  Pro  Lys  Glu  Ser
         275                      280                      285
Lys  Phe  Arg  Leu  Thr  Thr  Lys  Phe  Phe  Gly  Thr  Phe  Leu  Pro  Glu  Val
290                      295                      300                           305
Ala  Lys  Lys  Phe  Pro  Asn  Met  Lys  Ile  Gln  Ile  His  Val  Ser  Ala  Ser
                   310                      315                           320
Thr  Pro  Pro  His  Leu  Ser  Val  Gln  Pro  Thr  Gly  Leu  Thr  Phe  Tyr  Pro
              325                      330                      335
Ala  Val  Asp  Val  Gln  Ala  Phe  Ala  Val  Leu  Pro  Asn  Ser  Ser  Leu  Ala
         340                      345                      350
Ser  Leu  Phe  Leu  Ile  Gly  Met  His  Thr  Thr  Gly  Ser  Met  Glu  Val  Ser
         355                      360                      365
Ala  Glu  Ser  Asn  Arg  Leu  Val  Gly  Glu  Leu  Lys  Leu  Asp  Arg  Leu  Leu
370                      375                      380                           385
Leu  Glu  Leu  Lys  His  Ser  Asn  Ile  Gly  Pro  Phe  Pro  Val  Glu  Leu  Leu
                   390                      395                           400
Gln  Asp  Ile  Met  Asn  Tyr  Ile  Val  Pro  Ile  Leu  Val  Leu  Pro  Arg  Val
              405                      410                      415
Asn  Glu  Lys  Leu  Gln  Lys  Gly  Phe  Pro  Leu  Pro  Thr  Pro  Ala  Arg  Val
         420                      425                      430
Gln  Leu  Tyr  Asn  Val  Val  Leu  Gln  Pro  His  Gln  Asn  Phe  Leu  Leu  Phe
         435                      440                      445
Gly  Ala  Asp  Val  Val  Tyr  Lys
450                      455
```

( 2 ) INFORMATION FOR SEQ ID NO:3:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:3:

CGTATGGCCA GCACCTGAAC TCCT                      24

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GAGGGCTTTG TTGGAGA                            17

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Pro  Ala  Pro  Glu  Leu  Leu
1                     5

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CAGTTTAAAA CTCACACATG CCCACC                  26

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Lys  Thr  His  Thr  Cys  Pro  Pro  Cys
1                     5

( 2 ) INFORMATION FOR SEQ ID NO:8:

( i ) SEQUENCE CHARACTERISTICS:
        ( A ) LENGTH: 17 base pairs
        ( B ) TYPE: nucleic acid (C) STRANDEDNESS: single
(D) TOPOLOGY: linear (ii) MOLECULE TYPE: cDNA (xi) SEQUENCE DESCRIPTION: SEQ ID NO:8:

AGCTTCCCAG TTCCCAG 17

(2) INFORMATION FOR SEQ ID NO:9:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:9:

TATTTGGTC ATTACTGGCA GAGT 24

(2) INFORMATION FOR SEQ ID NO:10:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

GCACCTGCTA CTGACCGC 18

(2) INFORMATION FOR SEQ ID NO:11:

(i) SEQUENCE CHARACTERISTICS:
(A) LENGTH: 12 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:11:

GGTCAGTAGC AG 12

(2) INFORMATION FOR SEQ ID NO:12:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:12:

AAGCTTGTCG ACCAGGCCTT GAGGT 25

(2) INFORMATION FOR SEQ ID NO:13:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:13:

CTGGAGGCGG TGATGGTG                                                18

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CGAAACAAGA TGAACAGCCA GGTCTGCGAG                                   30

( 2 ) INFORMATION FOR SEQ ID NO:15:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CTCGCAGACC TGGCTGTTCA TCTTGTTT                                     28

( 2 ) INFORMATION FOR SEQ ID NO:16:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GCCACCRCCA TGG                                                     13

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

ACTGTCGACG CCACCATGGC CAGGGGC                                      27

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CCGCGGCTCG AGCTATATTT TGGTCAT                                      27

( 2 ) INFORMATION FOR SEQ ID NO:19:

( i ) SEQUENCE CHARACTERISTICS:
        ( A ) LENGTH: 6 amino acids
        ( B ) TYPE: Amino Acids
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Val Asn Pro Gly Val Val
6

BPI-IMMUNOGLOBULIN FUSION PROTEINS

This application is a continuation-in-part of U.S. patent application Ser. No. 07/885,911, filed May 19, 1992 now abandoned.

FIELD OF THE INVENTION

The present invention generally relates to recombinant hybrid fusion proteins useful in treating bacterial infection in humans, DNA sequences encoding such proteins, recombinant methods for preparing the proteins, and pharmaceutical preparations containing the recombinant products. Hybrid fusion proteins of the present invention are expression products of direct transcriptional fusions of DNAs encoding bactericidal/permeability-increasing protein or a biologically active fragment thereof and DNAs encoding one or more immunoglobulin heavy chain constant regions, which fusions have been incorporated into a suitable plasmid vector and transfected or transformed into a host cell. The recombinant-produced BPI-Immunoglobulin fusion protein expression products (hereinafter "rBPI-Ig") are useful as endotoxin binding proteins and as bactericidal agents.

BACKGROUND OF THE INVENTION

Bactericidal/permeability-increasing protein (hereinafter "BPI") is a cationic protein which binds to the lipid A portion of bacterial lipopolysaccharide (hereinafter "LPS"). Binding of the BPI protein to bacterial LPS increases the envelope permeability of susceptible gram negative bacteria. Ooi, et al., *J. Biol. Chem.*, 262:14891 (1987). BPI also binds to soluble LPS. Human BPI protein has been isolated from polymorphonuclear neutrophils (hereinafter "PMNs") by acid extraction combined with either ion exchange chromatography or *E. coli* affinity chromatography. Elsbach, et al. *J. Biol. Chem.*, 254:11000 (1979); Weiss et al., *Blood*, 69:652 (1987).

The holo-BPI protein isolated from human PMNs has potent bactericidal activity against a broad spectrum of gram-negative bacteria. Elsbach, et al., *J. Biol. Chem.*, 254:11000 (1979). This antibacterial activity appears to be associated with the amino terminal region of the isolated human holo-BPI protein. In contrast, the C-terminal region of the isolated human BPI protein displays only slightly detectable anti-bacterial activity. Ooi, et al., *J. Exp. Med.*, 174:649 (1991). Human DNA encoding BPI has been cloned and the amino acid sequence of the encoded protein has been elucidated. Gray et al., *J. Biol. Chem.*, 264:9505–9509 (1989); U.S. Pat. No. 5,198,541.

Immunoglobulins comprise a family of proteins with numerous structural similarities, but also important structural differences which result in differences in antigen binding properties and other biological activities. For example, the IgG isotype antibodies have the longest serum half life and are susceptible to placental transfer. The most potent anti-viral activity is associated with the IgA isotype antibodies; while the IgM isotype antibodies possess the greatest antibacterial efficacy. Stites, et al. *Basic and Clinical Immunology*, p. 32 (Appleton & Lange, 6th ed. 1987). Within each isotype of antibody in the immunoglobulin family there exist several subclasses and allotypic variations. Id.

Members of the so-called "immunoglobulingene superfamily" generally possess extracellular domains which are characterized by multiple looping due to the formation of disulfide bridges. Such looping occurs in the heavy chain constant domains, (designated CH1, CH2, CH3, and CH4) of immunoglobulin molecules. Non-immunoglobulin compounds possessing multiple looping domains which are homologous to those present in members of the immunoglobulin superfamily also exist and certain of these have been termed "adhesons". See, e.g., PCT Application No. WO89102922, published Apr. 6, 1989; Capon et al., *Nature*, 337:525–531 (1989).

Of particular interest to the present invention are reports of the recombinant synthesis of hybrid fusion proteins involving a portion of an adheson as the first component and an immunoglobulin heavy chain constant region as a second component of the fusion. See, e.g. Harris, *Eur. J. Biol. Chem.* 194:611–620 (1990) and Capon et al., supra, addressing the formation of CD4/IgG fusions. The structural design rationale for such a molecule is based on the observation that the adheson component of the fusion has a structure similar to that of the immunoglobulin component, and would therefore be expected to fold in a manner which is complementary to that of the immunoglobulin component. See Gascoigne, et al., *P.N.A.S.* (USA), 84:2936–2940 (1987) addressing recombinant chimeric T-cell receptor-immunoglobulin proteins. See also Mariuzza, et al., *J. Biol. Chem.*, 264(13) :7310–7316 (1989); Goverman, et al., *Cell* 60:929–939 (1990); Gregoine, et al. *P.N.A.S.* (USA), 88:8077–8081 (1991); Bismuth, et al., *Molecular Immunol.*, 27(11) :1127–1136 (1990) (addressing similar T-cell receptor-immunoglobulin fusions). A soluble CD44-immunoglobulin fusion protein has also been reported. Aruffo, et al., *Cell* 61:1303–1313 (1990).

Ashkenazi, et al., *P.N.A.S.*(USA), 88:1035 (1991) report protection against endotoxic shock through use of a chimeric immuno-adhesin protein (an adheson variant) which acts as a tumor necrosis factor (TNF) antagonist. The TNF antagonist reported therein is a hybrid fusion protein wherein the extracellular portion of a TNF receptor (TNFR) protein is fused to a constant domain of a human IgG heavy chain. This TNFR-IgG fusion reportedly binds to and blocks the cytotoxic effect of TNF on actinomycin-D treated cells and provides protection against endotoxin challenge when administered prior to the endotoxin.

Significantly, all of the fusion proteins described above have involved molecules that are expressed on the surface of cells as integral membrane proteins and, with the exception of CD44 and the TNF receptor, have possessed structures characteristic of the immunoglobulin gene superfamily.

Published PCT application WO92/03535 reports the construction of fusion of an amino-terminal portion of BPI to cDNA encoding the constant domain of IgG. However, that report fails to indicate how such protein-cDNA constructions are made and further fails to teach how many other types of BPI-Ig fusion may be constructed.

SUMMARY OF THE INVENTION

The present invention provides novel hybrid fusion proteins useful in treating bacterial infection and the sequelae thereof. Also provided are DNA sequences encoding such proteins, recombinant methods for preparing the proteins, and pharmaceutical preparations containing the recombinant products.

According to one aspect of the invention, hybrid fusion proteins are provided which, at their amino terminal, comprise a bactericidal/permeability-increasing protein or a biologically active fragment thereof fused to at least one constant domain of an immunoglobulin heavy chain or an allelic variant thereof which forms the carboxy terminal of the fusion protein.

In a preferred embodiment of the invention, the immunoglobulin heavy chain constant region portion of the fusion comprises two domains of the heavy chain constant region and most preferably the CH2 and CH3 domains. Fusion proteins of the present invention may also possess an immunoglobulin hinge region between the immunoglobulin and BPI regions.

Immunoglobulin heavy chain constant domains useful in formation of hybrid proteins of the present invention may be patterned after any isotype, but are preferably based on IgG, IgA, or IgM isotypes or allelic variants of those isotypes.

In presently preferred embodiments of the invention, hybrid fusion proteins comprise an amino terminal fragment including from 176 to 199 of the initial amino terminal residues of the mature human BPI protein. Also, the BPI portion of the fusion may comprise a BPI analog, wherein the cysteine residues at either or both of positions 132 and 135 of the native BPI sequence is replaced by another amino acid, preferably alanine or serine. When produced by recombinant methods, fusion proteins are isolated in monomeric or homodimeric forms.

According to another aspect of the invention, DNA sequences are provided which encode the above-described hybrid fusion proteins. Also provided are autonomously replicating DNA plasmid vectors including such DNA sequences and host cells stably transformed or transfected with such DNA sequences in a manner allowing their expression. DNA which confers optimized expression of the protein product are preferred for incorporation into rBPI-Ig fusion vectors. Transformed host cells of the invention are of manifest utility in procedures for the large-scale production of the fusion proteins involving the cultured growth of the hosts in a suitable medium and the isolation of the proteins from the cells or their growth medium.

The invention also provides novel pharmaceutical compositions comprising hybrid fusion proteins according to the invention together with pharmaceutically acceptable diluents, adjuvants, and carriers. The compositions are, in turn, useful for treatment of Gram negative bacterial infections and the sequelae thereof including endotoxin related shock and one or more conditions associated therewith such as disseminated intravascular coagulation, anemia, thrombocytopenia, leukopenia, adult respiratory distress syndrome, renal failure, hypotension, fever, and metabolic acidosis. Providing the BPI protein or protein fragment or analog protein as part of a fusion with an immunoglobulin (Ig) heavy chain constant region provides the potential advantages of Fc receptor binding, bivalent binding to LPS, complement binding, and increased placental transfer.

A problem encountered in the preparation of pharmaceutical-grade BPI products is the formation of macroscopic particles which may decrease the homogencity and activity of the product. Therefore, preferred pharmaceutical composition containing rBPI-Ig fusion proteins comprise the combination of a poloxamer (polyoxypropylene-polyoxyethylene block copolymer) surfactant and a polysorbate (polyoxyethylene sorbitan fatty acid ester) surfactant. Such combination are taught in co-pending, co-owned U.S. patent application Ser. No. 08/012,360 by McGregor to have synergistic effects in stabilizing pharmaceutically-active polypeptides against particle formation. Most preferred is a composition in which the rBPI-Ig fusion is present in a concentration of 1 mg/ml in citrate buffered saline (0.02M citrate, 0.15M NaCl, pH 5.0) comprising 0.1% by weight of poloxamer 188 (Pluronic F-68, BASF Wyandotte, Parsippany, N.J.) and 0.002% by weight of polysorbate 80 (Tween 80, IcI Americas Inc., Wilmington, Del.).

Numerous additional aspects and advantages of the invention will become apparent to those skilled in the art upon considering the following detailed description of the invention which describes presently preferred embodiments thereof.

DETAILED DESCRIPTION

Figure 1:
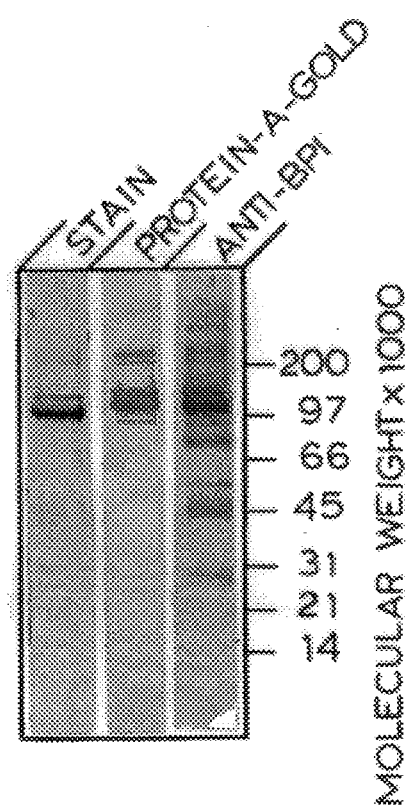
FIG. 1 demonstrates the results of SDS-PAGE performed on the eluate from columns containing fusions according to the invention.

The following detailed description addresses the manufacture of BPI-Ig fusion proteins according to the present invention. More specifically, Example 1 relates to the construction of DNA sequences for expression of various rBPI-Ig fusion proteins according to the present invention. Example 2 relates to the incorporation of DNAs of Example 1 into host cells and expression of encoded proteins. Example 3 relates to production, scale up, and isolation of fusion proteins according to the invention. Example 4 provides immunological and activity-based characterizations of fusion proteins according to the invention. Example 5 provides properties of fusion proteins according to the invention, including binding properties, pharmacokinetic properties, and in vivo properties.

EXAMPLE 1

Construction of rBPI-Ig Expression Vectors

A. Construction of Vectors for Expression of rBPI-Ig Fusion Proteins Involving IgG Regions Several vectors were constructed for expression of hybrid fusion proteins. These generally consisted of direct transcriptional fusions between DNAs encoding portions of BPI and one or more domains of a human immunoglobulin gamma-1 heavy chain constant region (IgG$_1$ HC; Fc region). These vectors differed in the exact locations of the junctions between the BPI and IgG-encoding sequences.

Plasmid vectors described herein for the expression of rBPI-Ig fusion proteins in mammalian cells were constructed based on vectors (e.g., pING2227) that were originally developed for expression of immunoglobulin heavy chain genes. The construction of pING2227 is described in Robinson et al., *Hum. Antibod. Hybridomas* 2:84–93, (1991). That vector contains the following features: the mouse immunoglobulin heavy chain enhancer element, the LTR enhancer-promoter from mouse Abelson virus DNA, the SV40 16S splice junction at the 5' end of the gene to be expressed, and the human genomic gamma-1 polyadenylation sequence at the 3' end. The vector has SalI and SstII cloning sites into which the gene to be expressed may be inserted. The vector also contains a selectable marker (neo) under the control of the SV40 early promoter, and sequences of pBR322 necessary for growth in E. coli. The vector pING2237N, which was derived from pING2227, contains a unique NotI site introduced at the unique AatII site in the pBR322-derived sequence of pING2227. Instead of the neo selectable marker gene, pING2237N contains an altered mouse dihydrofolate reductase ("DHFR") gene sequence as described by Simonsen et al. P.N.A.S. (USA), 80:2495–2499 (1983). Plasmid pMB27, employed in certain of the rBPI-Ig constructions described below, is essentially identical to pING2237N, incorporating a DNA insert specifying the heavy chain coding region of chimeric H65, an antibody directed against CD5 consisting of a mouse variable region and a human IgG1 constant region.

The expression vector, pING4503, was used as a source of DNA encoding a recombinant expression product designated "rBPI(1-199), i.e., a polypeptide having the 31-residue signal sequence and the first 199 amino acids of the N-terminus of the mature human BPI as set out in SEQ ID NOS: 1 and 2 except that valine at position 151 is specified by GTG rather than GTC and residue 185 is glutamic acid (specified by GAG) rather than lysine (specified by AAG). The BPI product designated "rBPI (1-199)" herein has previously been referred to as "rBPI-23" and the holo-rBPI protein has previously been referred to as "rBPI-50". See, e.g., Gazzano-Santoro, et al., Infection and Immunity, 60:4754–4761 (1992); co-owned, co-pending U.S. patent application Ser. No. 07/885,911. The BPI-encoding DNA in pING4503 is inserted into unique SalI and SstII sites in the vector. Plasmid pING4503 is otherwise identical to pING2237N except that pING4503 contains a gpt selectable marker instead of DHFR.

Two vectors, plasmid pING4511 and plasmid pING4512, were designed for fusion of DNA encoding 30 bp of the 5' untranslated region, the signal sequence and the first 191 amino acids of human BPI at an in-frame, blunt junction with IgG HC DNA sequences.

1. Construction of pING4511

To construct pING4511, plasmid pING4503 was cut with AlwNI, the ends were made blunt with T4 DNA polymerase, and the DNA was then cut with SalI. The resultant ~700 bp SalI/blunt DNA fragment contained the 30 bp 5' untranslated sequence and the DNA encoding the signal and first 191 amino acids of BPI and was gel purified. IgG HC sequences were PCR amplified from plasmid pMB27 (described above) using the following primers:

(1) Primer CH2-Msc having the sequence,
5'-CGTATGGCCAGCACCTGAACTCCT-3' (SEQ. I.D. NO. 3.) was designed for top strand amplification and to introduce an MscI site (TGGCCA) at the 5' end of the CH2 region amplified.

(2) Primer KAO-3 having the sequence,
5'-GAGGGCTTTGTTGGAGA-3', (SEQ. I.D. NO. 4) was designed for bottom strand amplification commencing with the sequence downstream (3') of an SstII site of IgG HC within pMB27.

PCR amplification was accomplished using the GeneAmp PCR Kit (Perkin-Elmer Cetus, Norwalk, Conn.), according to the manufacturer's protocols. A typical PCR amplification reaction was carried out for 30 cycles consisting of 1 minute denaturation at 94° C., 2 minutes annealing at 55° C., 3 minutes extension at 72° C., followed by a final 10 minute extension at 72° C. The DNA amplified with the primers described above was digested with MscI and SstII, and the resulting approximately 185 bp fragment was gel purified. The 5' (blunt) end of this fragment was designed to correspond to the sequence "PAPELL . . .", (SEQ ID NO: 5) located at the 5' end of the CH2 domain of the IgG HC, immediately after the hinge region; the 3' end corresponds to the unique SstII site within the CH2 domain. This fragment was then ligated together with the SalI/blunt, BPI DNA fragment (described above) into the SalI/SstII digested vector fragment from pMB27 to generate plasmid pING4511. Upon sequencing across the blunt BPI-IgG junction in pING4511, however, it was discovered that the MscI site had not been digested and that, therefore, the IgG portion of the fusion protein was not in the same translational reading frame as the BPI portion. This plasmid was therefore not used for transfection of mammalian cells, but was used as a source of fragments in the construction of other vectors described below.

2. Construction of pING4512

A strategy similar to that employed for construction of pING4511 was used to construct pING4512, including fusion of the DNA sequence encoding 30 bp of 5' untranslated region, the signal and the first 191 amino acids of BPI with IgG HC sequences, which also included the hinge region of the IgG HC. The IgG portion was PCR amplified from pMB27 using the primers KAO,3 and primer CH2-2C-Dra having the sequence: 5'-CAGTTTAAAACTCACACATGCCCACC-3' (SEQ. I.D. NO. 6) and designed to introduce a DraI site (TTTAAA) at the 5' end of the amplified fragment. The amplified PCR fragment was digested with DraI and SstII and the resulting approximately 210 bp fragment was gel purified. The 5' (blunt) end of this fragment was designed to correspond to the sequence "KTHTCPPC . . ." (SEQ. I.D. NO. 7) (i.e., 4 residues upstream of the hinge region of the IgG heavy chain); the 3' end corresponds to the unique SstII site within the CH2 domain. This fragment was then ligated together with the ~700 bp SalI/blunt BPI fragment from pING4503 (described above) into the SalI/SstII-cut vector fragment from pMB27 to generate pING4512. Upon sequencing across the blunt BPI-IgG junction in pING4512, it was discovered that the DraI site had not been digested. The IgG portion was, however, maintained in the same reading frame as the BPI portion with the insertion of the sequence 5'-CAGTTT-3', coding for the amino acids Gln-Phe, at the junction between BPI and IgG HC. Plasmid pING4512 was deposited with the American Type Culture Collection, 12301 Parklawn Drive, Rockville, Md. 20852 USA on May 12, 1992, under accession number ATCC 75239.

3. Construction of pING4514 and pING4515

Two rBPI-IgG fusion vectors, plasmids pING4514 and pING4515, were constructed containing the 30 bp 5' untranslated sequence, a signal sequence, and the initial 199 amino terminal amino acids of human BPI fused to IgG sequences. This was accomplished by PCR amplification of the 3' end of the BPI fragment DNA insert within pING4503 using the primers BPI-5: 5'-AGCTTCCCAGTTCCCAG-3' (SEQ. I.D. NO. 8) located within the first 199 amino acids of the mature BPI sequence, and BPI-11:5'-

TATTTTGGTCATTACTGGCAGAGT-3' (SEQ. I.D. NO. 9) corresponding to the 3' end of the BPI fragment sequence (i.e. through residue 199). The resulting PCR fragment was cut with BstBI, (a site within the BPI coding region that is unique in the vector) and the 100 bp DNA fragment representing the 3' end of the BPI amino terminal fragment through amino acid 199 was then purified. To construct pING4514, representing the fusion of BPI fragment DNA with IgG HC without an immunoglobulin hinge region, the following three fragments were ligated together: the 100 bp BstBI/blunt BPI 3' end fragment, the MscI-SstII IgG HC fragment from pING4511 and the BstBI-SstII vector fragment from pING4511. Plasmid pING4514 was deposited with the American Type Culture Collection, 12301 Parklawn Drive, Rockville, Md. 20852 USA on May 12, 1992, under accession number ATCC 75240. To construct pING4515, representing the fusion of BPI fragment DNA to IgG HC sequences which includes the hinge region, the following 3 fragments were ligated together: the 100 bp BstBI-blunt rBPI(1–199) 3' end fragment; the DraI/SstII IgG HC fragment from pING4512; and the BstBI-SstII fragment from vector pING4511. Plasmid pING4515 was deposited with the American Type Culture Collection, 12301 Parklawn Drive, Rockville, Md. 20852 USA on May 12, 1992, under accession number ATCC 75241.

4. Construction of pING4528

A BPI-IgG fusion vector was constructed in which the BPI signal sequence was placed in front of the region encoding residues 61–191 of rBPI (i.e., involving deletion of residues 1–60 of mature BPI) and then fused to DNA encoding the hinge-CH2-CH3 domains of IgG HC. To obtain the fragment encoding the BPI signal sequence, pIC110, a plasmid containing the same BPI DNA insert as in pING4503, flanked by SalI and SstII sites at the 5' and 3' ends, respectively, and cloned into the SmaI site of pT7T3 18U (Pharmacia, Uppsala, Sweden), was digested with EagI. The ends were made blunt with T4 DNA polymerase, and the DNA was then digested with SalI. The resulting approximately 123 bp SalI/blunt fragment representing 30 bp of 5' untranslated DNA and the BPI signal sequence was gel purified. Plasmid pING4512 (described above) was used to obtain a fragment containing the coding region of residues 61–191 of BPI fused to IgG HC sequences. pING4512 was digested with EcoRI to cut the BPI sequence at the region encoding residues 60–61 (Glu-Phe, GAATTC). This resulted in a 5' overhang of 4 bp: AATT. To make the 5' end of this fragment blunt and in frame beginning at residue 61 (Phe, TTC), the 3' recessed end of the bottom strand was filled in with T4 DNA polymerase in the presence of deoxyadenosine triphosphate only, leaving a 2 base pair 5' overhang of AA. This 5' overhang was removed by treatment with mung bean nuclease to develop the desired blunt end. The desired rBPI-Ig-encoding DNA fragment, including some 3' flanking vector sequence, was then excised from the vector by cutting with DraIII, a unique site located in the 3' polyadenylation region. The resulting blunt/DraIII 1963 bp fragment was gel purified. pING4528 was then constructed by ligating the following 3 fragments: the approximately 123 bp SalI/blunt BPI signal sequence fragment, the blunt/DraIII rBPI-Ig containing fragment, and the SalI/DraIII vector fragment from pING4506 (a plasmid essentially similar to rBPI expression vector pING4503 described above, but containing a gpt marker).

5. Construction of Other Vectors

The vectors described above, pING4511, pING4512, pING4514, and pING4515, all contain the mouse dihydrofolate reductase (DHFR) gene as the selection marker. Similar vectors may be constructed comprising rBPI-IgG fusions with other selectable markers. For example, pING4529 contains a DNA insert identical to the insert contained in pING4512, but the vector contains the gpt selection marker instead of DHFR.

Other vectors for expression in mammalian cells, representing fusions of DNA encoding BPI sequences and DNA encoding IgG heavy chain sequences, may be constructed using methods as described herein. For example, the BPI portion of the fusion may include deletions of any part of the BPI sequence, other than those specifically described herein. Additionally, portions of the BPI sequence may be otherwise replaced, varied or mutated, or combinations thereof may be employed. The IgG portion may consist of any part of the sequence of the heavy chain constant region.

B. Construction of Vectors for Expression of rBPI-Ig Fusion Proteins Involving IgM Regions Plasmid pJB123 containing human IgM heavy chain genomic DNA cloned in pBR322 was used as the source of IgM HC constant region DNA sequences. The DNA sequence of human IgM HC constant region was obtained from the EMBL database, accession number X14940. A 1672 bp PstI fragment was excised from pJB123 (obtained from P. Leder) and was subcloned into the PstI site of plasmid pT7T3 18U (Pharmacia) to generate plasmid pIC1O9. The excised PstI fragment included the portion of the DNA sequence of IgM HC beginning at the 3' end of the intron immediately preceding the CH2 domain and extending into the intron located between the CH4 domain and the first membrane exon of the IgM sequence. The excised PstI sequence further encoded exons coding for CH2, CH3, and CH4 domains of IgM HC, including the intervening sequences. The portion of the IgM DNA sequence which was used in the construction of the rBPI-IgM fusion vector was obtained as follows. Plasmid pIC1O9 was cut with PstI. The ends were made blunt with T4 DNA polymerase, then the 3' end of the insert was cut with BanI. The resulting 1456 bp fragment that resulted was gel purified. The 5' blunted end of that fragment included an additional GTG, coding for valine, in front of the coding region of the CH2 exon. The BanI digest at the 3' end of the fragment cut the DNA 11 base pairs upstream of the termination codon located at the end of the CH4 exon. In order to reconstruct the 3' end of CH4 and put in an SstII site to facilitate cloning into the mammalian expression vector, two complimentary oligonucleotides were synthesized: "IgM-BS link" having the sequence, 5'-GCACCTGCTACTGACCGC-3' (SEQ. I.D. NO. 10) and "IgM-SB link" having the sequence 5'-GGTCAGTAGCAG-3', (SEQ. I.D. NO. 11). Annealing of these two oligonucleotides generated a small linker fragment with BanI and SstII sticky ends. To generate the final expression vector, the blunt/BanI IgM fragment (containing the CH2, CH3, and CH4 regions) and the BanI/SstII linker fragment were ligated together with the 100 bp BstBI/blunt BPI 3' end fragment (as in part A, 3 above) into the BstBI-SstII vector fragment from pING4506, an expression vector incorporating a DNA insert specifying the signal peptide and rBPI (1–199) residues, and including the gene for gpt selection. The resultant vector was designated pING4517. Plasmid pING4517 was deposited with the American Type Culture Collection, 12301 Parklawn Drive, Rockville, Md. 20852 USA on May 12, 1992, under accession number ATCC 75242

C. Construction of Vectors for Expression of rBPIala$^{132}$-Ig Fusion Proteins Expression vectors were constructed comprising a BPI N-terminal fragment wherein a cysteine at residue 132 was replaced by an alanine. Recombinant-produced analogs of this type are generically designated "rBPIala$^{132}$" and a fusion protein comprising such an analog fused to a constant region of an immunoglobulin heavy chain is generically designated "rBPIala$^{132}$-Ig." Three vectors were constructed for expression of rBPIala$^{132}$-IgG fusion proteins, wherein the rBPIala$^{132}$ portion of the fusion comprised the first 191 or 176 amino acids of the BPI N-terminal (designated "rBPI(1–191)ala$^{132}$-Ig" and "rBPI(1–176)ala$_{132}$", respectively).

1. Construction of pING4531

To obtain pING4531, which contains rBPI(1–191)ala$^{132}$ fused to a constant domain of an IgG heavy chain, plasmid pING4519 was first constructed. The construction of pING4519 is fully described in co-owned, co-pending U.S. patent application Ser. No. 08/013,801 by Theofan. Briefly, a PvuII site (CAGCTG), which occurs only once in the DNA encoding rBPI(1–199) and which is located between the cysteine residues at positions 132 and 135, was utilized to construct pING4519. DNA encoding the BPI(1–199) fragment, including a 31 amino acid signal sequence, was obtained by SalI and SstII digestion of pING4503, a vector containing the BPI(1–199) fragment between unique SalI and SstII sites, the mouse immunoglobulin heavy chain enhancer element, the LTR enhancer-promoter element from Abelson murine leukemia virus (A-MuLv) DNA, the SV40 19S/16S splice junction at the 5' end of the gene to be expressed, and the human genomic gamma-1 polyadenylation site at the 3' end of the gene to be expressed.

The SalI-SstII fragment containing BPI(1–199) was purified and digested with PvuII, resulting in an approximately 529 bp SalI-PvuII fragment and an approximately 209 bp PvuII-SstII fragment, each of which was purified separately.

Plasmid pING4519 contains a BPI-encoding insert in which the codon for cysteine at position 132 is replaced by a codon for alanine at that position. In order to generate that substitution, BPI-encoding sequences described above were PCR-amplified using the primers BPI-6, AAGCTTGTC-GACCAGGCCTTGAGGT (SEQ ID NO: 12) and BPI-14, CTGGAGGCGGTGATGGTG (SEQ ID NO: 13), which incorporated the base substitution necessary to encode an alanine at position 132. PCR amplification was accomplished using the Gene Amp PCR kit (Perkin Elmer Cetus, Norwalk, Ct.) according to the manufacturer's instructions. The resulting PCR fragment was digested with SalI, resulting in a 529 bp SalI blunt fragment which was ligated with the approximately 209 bp PvuII-SstII fragment described above and the large vector fragment resulting from SalI-SstII digestion of pING4503 to generate pING4519.

The plasmid of interest, pING4531, was then constructed by digesting pING4519 with AlwNI, treating with T4 polymerase, and digesting with SalI to generate an approximately 700 bp fragment which contained residues 1–191 of rBPI(1–199)ala$^{132}$. Next, an approximately 1565 bp fragment which contained the immunoglobulin portion of the fusion and additional downstream vector sequences was generated from pING4512 by digestion with DraI and DraIII. Finally, pING4513 was digested with DraIII and SalI and the large vector fragment containing the gpt marker was purified. The three vector fragments described above were ligated together to produce pING4531.

2. Construction of pING4534 and pING4535

Plasmid pING4534 contains a BPI-Ig fusion comprising a truncated form of rBPI which includes the initial 176 amino acids of the BPI N-terminus and in which the substitution of alanine for the cysteine at position 132 is present (designated "rBPI(1–176)ala$^{132}$). Further, pING4534 contains only the CH2 and CH3 domains of an IgG heavy chain. In order to generate the truncated rBPI(1–176)ala$^{132}$ analog, DNA encoding rBPI(1–199) was digested with BstBI, which cuts after amino acid 167. The additional BPI sequences (i.e., amino acids 168–176) were replaced by using two annealed complementary oligonucleotides, BPI-24, 5'-CGAAACAAGATGAACAGCCAGGTCTGCGAG-3' (SEQ ID NO: 14) and BPI-25, 5'-CTCGCAGACCTGGCTGTTCATCTTGTTT-3' (SEQ ID NO: 15).

A vector, pING4534, comprising DNA encoding rBPI(1–176)ala$^{132}$-Ig fusion protein was constructed by ligating an SstII-BstBI fragment from pING4531 containing all the vector seqeunces and DNA encoding rBPI(1–176)ala$^{132}$, an approximately 186 bp MscI-SstII fragment from pING4511 and the BstBI-blunt fragment generated by annealing BPI-24 and BPI-25.

Plasmid pING4535 is identical to pING4534 except that it also includes the immunoglobulin hinge region. Plasmid pING4535 was constructed using 3 fragments—the SstII-BstBI vector and BPI-containing fragment from pING4531, an approximately 210 bp DraI-SstII immunoglobulin-encoding fragment from pING4512, and a BstBI-blunt fragment generated by annealing BPI-24 and BPI-25.

D. Construction of Optimized Vectors for Expression of rBPI-Ig Fusion Proteins

1. Construction of rBPI-Containing Vectors having Elements for Optimized Expression Plasmids were constructed which contained DNA sequences useful for optimized expression of rBPI-Ig fusion proteins. In order to do so, several plasmids previously disclosed in co-owned, co-pending U.S. patent application Ser. No. 08/013,801 by Theofan, et al. were used as sources of elements for optimized expression of fusion proteins. Such elements include, but are not limited to, an optimized Kozak translation initiation sequence and mouse light chain transcription termination sequences.

Plasmid pING4533 contains rBPI(1–199)ala$^{132}$ with the initiating ATG in the context of the consensus Kozak translation initiation sequence, GCCACCRCCATGG (SEQ ID NO: 16) [Kozak, *Nucl. Acids Res.*, 15:8125 (1982)]. That vector was made by PCR amplification of BPI sequences from a plasmid containing the full-length BPI cDNA [in pGEM-7zf(+)] using the PCR primer BPI-23: ACTGTC-GACGCCACCATGGCCAGGGGC (SEQ ID NO: 17), incorporating a salI restriction side and the nucleotides GCCACC in front of the ATG (methionine) at position -27 of the BPI signal, and the primer BPI-2: CCGCGGCTC-GAGCTATATTTTGGTCAT (SEQ ID NO: 18), corresponding to the 3' and of the rBPI (1–199) coding sequence.

The approximately 700 bp PCR amplified DNA was digested with SalI and EcoRI and the resulting 270 bp fragment, including approximately the first third of the BPI(1–199) coding sequence, was purified. That SalI-EcoRI fragment was ligated to two other fragments: (1) a 420 bp EcoRI-SstII fragment from pING4519, encoding the remainder of BPI(1–199) wherein alanine replaces cysteine at position 132; and (2) an approximately 800 bp SstII-SalI vector fragment from pING4502 (a vector essentially similar to pING4503 except that it does not include the 30 bp 5' untranslated sequence and has a gpt marker rather than a DHFR marker), to generate pING4533 which contains a gpt marker.

Another series of vectors was also constructed which contained elements used in the construction of vectors containing BPI-Ig fusions for optimized expression of the gene product. Those vectors were based on pING4537, a vector essentially similar to pING4533 but which includes human light chain polyadenylation sequences and mouse light chain transcription termination sequences instead of the human heavy chain sequences in pING4533. The mouse kappa 3' sequences were obtained from pING3170, an expression vector which encodes a human light chain cDNA and includes a mouse genomic light chain 3' transcription termination sequence. This was accomplished by digesting with SstI, which cuts 35 bp upstream of the mouse light chain stop codon, treating with T4 DNA polymerase to make the end blunt, then cutting with BamHI, and purifying an approximately 1350 base pair fragment which includes the mouse kappa 3' sequences. The resulting fragment consisted of approximately 250 bp of the 3' portion of the human light chain constant region cDNA and the polyadenalation signal followed by a BamHI linker as described in the construct called Δ8 in Lui, et al. *J. Immunol.* 139:3521 (1987). The remainder of the approximately 1350 base pair fragment consists of a BglII-BamHI mouse kappa 3' genomic fragment, which is fragment "D" of Xu, et al., *J. Biol. Chem.*, 261:3838 (1986), and which supplies transcription termination sequences. That fragment was used in a three-piece ligation with two fragments from pING4533—the 3044 base pair fragment which includes all of the BPI insert and part of a vector obtained by digestion with SstII, T4 polymerase treatment, and NotI digestion, along with an approximately 4574 bp BamHI-NotI fragment. The resulting vector, pING4537 is identical to pING4533 with the exception of the above-noted differences in the genomic 3' untranslated region.

Additional vectors containing the kappa 3' untranslated sequences were constructed using pING4537 as the source of the kappa 3' fragment. Such a fragment was isolated by digestion of pING4537 with XhoI (which cuts at a unique XhoI site occuring immediately after the BPI stop codon) and BamHI. The resulting approximately 1360 bp XhoI-BamHI fragment was used in a series of three-piece ligations to generate two vectors, both of which contain the optimized Kozak translation initiation sequence at residue -27 of the signal sequence. The first of these vectors, pING4143, contains the gpt marker and was obtained by ligating the 4574 bp BamHI-NotI fragment from pING4223 with the NotI-XhoI BPI insert-containing fragment of approximately 3019 bp and the pING4537 XhoI-BamHI fragment. A second vector, pING4146, contained the DHFR marker and was obtained by ligating a pING4222 approximately 4159 base pair BamHI-NotI fragment with a pING4223 NotI-XhoI BPI insert-containing fragment of approximately 3019 base pairs, and the XhoI-BamHI fragment of pING4537.

2. Construction of Vectors for Expression of rBPI-Ig Fusion Proteins

Expression vectors comprising DNA encoding rBPI-Ig fusion proteins were constructed which include elements leading to optimized expression of the fusion utilizing the plasmids described in the section immediately above.

The first of these vectors, pING4156, includes the identical BPI-encoding region as in pING4512 and was constructed using vector fragments from three other constructions:

1) A 270 bp SalI-EcoRI fragment from pING4143, which included the Kozak sequence and approximately the first one-third of the BPI coding region;

2) Vector sequences from pING4143 obtained by digestion with XhoI, blunt-ending with T4 polymerase, and cutting with SalI; and 3) The approximately 1092 bp EcoRI-NaeI fragment from pING4512, containing the rest of the BPI sequence through amino acid 191 and the immunoglobulin sequences.

The second such vector, pING4157, which contains a DNA insert encoding rBPI(1-176) fused to an immunoglobulin hinge-CH2-CH3 region, was assembled from a three-piece ligation. The first piece was a 590 bp SalI-BstBI fragment from pING4145 (a vector essentially identical to pING4143, described above, except that it contains the wild type cysteine at position 132). That piece was ligated to vector sequences obtained from XhoI digestion of pING4145 which were blunted with T4 polymerase and cut with SalI. The third piece of the ligation was an approximately 720 bp BstBI-NaeI fragment from pING4535. While both pING4156 and pING4157 possess the gpt marker, constructions containing other markers, such as his or DHFR, may be constructed according to known techniques, including those described in the previous subsection. Two such vectors are pING4158 and pING4159, which are identical to pING4156 and pING4157, respectively except that both pING4158 and pING4159 contain a DHFR marker instead of gpt.

A summary of all of the foregoing vector constructions which contain an rBPI-Ig fusion protein is provided below in Table 1.

TABLE 1

Summary of Constructions Comprising BPI-Ig Fusions

| Plasmid | BPI Fragment | Immunoglobulin Fragment | Selectable Marker | Sequence at Junction | Other |
|---|---|---|---|---|---|
| pING4512 | 1–199 | IgG hinge-CH2—CH3 | DHFR | ...QPYFQ:QF:KTHT CPPCPAPELL... | Heavy chain 3' UT, Natural 5' UT |
| pING4514 | 1–199 | IgG CH2—CH3 | DHFR | ..VMTKI: :PAPELL... | Heavy chain 3' UT, Natural 5' UT |
| pING4515 | 1–199 | IgG hinge-CH2—CH3 | DHFR | ...VMTKI: :KTHTCPPCPAPEL L... | Heavy chain 3' UT, Natural 5' UT |
| pING4517 | 1–199 | IgM CH2—CH3—CH4 | gpt | ...VMTKI:V:IAELP P | Heavy chain 3' UT, Natural 5' UT |
| pING4528 | 61–191 | IgG hinge-CH2—CH3 | gpt | ...QPYFQ:QF:KTHT | Heavy chain 3' |

TABLE 1-continued

Summary of Constructions Comprising BPI-Ig Fusions

| Plasmid | BPI Fragment | Immunoglobulin Fragment | Selectable Marker | Sequence at Junction | Other |
|---------|--------------|-------------------------|-------------------|----------------------|-------|
|         |              |                         |                   | CPPCPAPELL...        | UT, Natural 5' UT |
| pING4529 | 1–191 | IgG hinge-CH2—CH3 | gpt | ...QPYFQ:QF:KTHT CPPCPAPELL... | Heavy chain 3' UT, Natural 5' UT |
| pING4531 | 1–191ala$^{132}$ | IgG hinge-CH2—CH3 | gpt | ...QPYFQ:QF:KTHT CPPCPAPELL... | Heavy chain 3' UT, Natural 5' UT |
| pING4534 | 1–176ala$^{132}$ | IgG CH2—CH3 | gpt | ...SQVCE: :PAPELL | Heavy chain 3' UT, Natural 5' UT |
| pING4535 | 1–176ala$^{132}$ | IgG hinge-CH2—CH3 | gpt | ...SQVCE: :KTHTCPPCPAPEL L | Heavy chain 3' UT, Natural 5' UT |
| pING4156 | 1–191 | IgG hinge-CH2—CH3 | gpt | ...QPYFQ:QF:KTHT CPPCPAPELL | Light chain 3' UT optimized Kozak sequence |
| pING4157 | 1–176 | IgG hinge-CH2—CH3 | gpt | ...SQVCE: :KTHTCPPCPAPEL L | Light chain 3' UT optimized Kozak sequence |
| pING4158 | 1–191 | IgG hinge-CH2—CH3 | DHFR | ...QPYFQ:QF:KTHT CPPCPAPELL | Light chain 3' UT optimized Kozak sequence |
| pING4159 | 1–176 | IgG hinge-CH2—CH3 | DHFR | ...SQVCE: :KTHTCPPCPAPEL L | Light chain 3' UT optimized Kozak sequence |

EXAMPLE 2

A. Transfection of CHO Cells for Production of rBPI-IgG Fusion Proteins

Mammalian cells are preferred host cells for production of proteins of the invention because such cells allow secretion and proper folding of heterodimeric and multimeric proteins and provide post-translational modifications such as pro-sequence processing and glycosylation.

Mammalian cells which may be useful as hosts for the production of rBPI-IgG fusions include cells of lymphoid origin, such as the hybridoma Sp2/O-Ag14 (ATCC CRL 1581) and cells of fibroblast origin, such as Vero cells (ATCC CRL 81), CHO-K1, CHO-DXB11, or CHO-DG44. The latter cell line (a DHFR$^-$ mutant of CHO Toronto obtained from Dr. Lawrence Chasin, Columbia University) was maintained in Ham's F12 medium plus 10% fetal bovine serum supplemented with glutamine/penicillin/streptomycin (Irvine Scientific, Irvine, Calif.).

CHO-DG44 cells were transfected with linearized pING4512, pING4514 or pING4515 DNA (40 μg, digested with PvuI, phenol-chloroform extracted and ethanol precipitated) using the calcium phosphate method of Wigler, et al., Cell, 11:223 (1977). Following calcium phosphate treatment, the cells were plated in T75 flasks and transfectants were obtained by growth in selective medium consisting of an αMEM medium lacking nucleosides (Irvine Scientific) and supplemented with dialyzed fetal bovine serum (100 ml serum dialyzed using 4L cold 0.15 NaCl using 6000–8000 cutoff for 16 hours at 4° C.). Untransfected CHO-DG44 cells are unable to grow in this medium because they possess the DHFR$^-$ mutation and were removed during successive feedings with the selective medium. At 1.5–2 weeks, only microcolonies consisting of transfected cells were observed. For pING4512 and pING4514, the transfected cells were removed from the flasks by trypsinization and subcloned by limiting dilution in 96 well plates. For pING4515, the transfected cells were grown as a mixed culture in selective medium supplemented with 0.1 μM methotrexate. Methotrexate-resistant cells were then removed from the flasks by trypsinization and subcloned by limited dilution in 96 well plates.

Subclones were analyzed for the presence of IgG-reactive protein in culture supernatants by anti-gamma ELISA. In this assay, Immulon-II 96 well plates (Dynatech) were pre-coated with goat α-human gamma antiserum. Supernatant samples where then added and peroxidase-labeled goat anti-human gamma antiserum was used for detection of bound α human gamma-reactive protein. For pING4512 and pING4515 transfectants, the 15 most productive positive clones were expanded in selective αMEM medium. The pING4512 transfectants were then grown on selective medium supplemented with 0.1 μM methotrexate. For pING4514 transfectants, the best producing 15 positive clones were expanded in selective αMEM medium supplemented with 0.1 μM methotrexate. Productivity of the subclones was reassessed in extinct 48-well cultures by α-gamma ELISA. In the case of the pING4512 and pING4515 transfectants, the best isolates secreted about 5 and 10 μg/ml, respectively, based on the gamma ELISA. The single best subclone for the pING4514 transfectants secreted about 10 μg/ml by the gamma ELISA. Supernatants for the best pING4512 subclones as determined by the gamma ELISA were also positive in an anti-BPI ELISA. Three isolates from each of the pING4512 and the pING4515 transfectants and four isolates from the pING4514 transfectants were chosen for further study. The best producing subclone in each of these groups was scaled up for production of rBPI-IgG fusion proteins. The best producers were pING4512 (Clone 100M, strain C1551), pING4514 (Clone 8D7, strain C1552), and pING4515 (Clone 4E6, strain C1549). These three cell lines were deposited with the American Type Culture Collection, 12301 Parklawn Drive, Rockville, Md. 20852 USA, on May 12, 1992 under acces-

EXAMPLE 3

A. Scale-up Growth and Production of BPI-IgG Fusion Proteins in Roller Bottles Growth in roller bottles was used for production of cells containing the rBPI-IgG fusions. The growth, isolation, and assay procedures which follow were performed using plasmid pING4512 and are presented here for exemplification. Similar procedures may be used for other plasmids according to the invention as would be apparent to one of ordinary skill in the art. For each roller bottle, a T150 flask (containing 50 ml of αMEM without nucleosides and 10% dialyzed fetal bovine serum) was inoculated with transfected cells and the cells were grown to confluence (~3–4 days). The cells were then trypsinized and transferred into a 900 $cm^2$ roller bottle containing 500 ml Ham's F12 media and 10% fetal bovine serum and grown to confluence (~3 days). Once confluency was reached, the Ham's F12 medium was removed and replaced with 500 ml HB-CHO serum-free medium (Irvine Scientific, Irvine Calif.). It had previously been found that optimal purification of recombinant BPI fragments from roller bottles was achieved by adding sterile S-Sepharose beads (Pharmacia, fast-flow #17-0511-01) to the HB-CHO medium in the roller bottles as described in co-owned, co-pending, concurrently filed U.S. patent application, Ser. No. 07/885,501 by Grinna (See also co-owned, concurrently-filed U.S. patent application Ser. No. 08/072,063), the disclosures of which are incorporated by reference herein. The beads were first washed and autoclaved (20 minutes, 121° C. and 10 ml aliquots) and were then added aseptically to the HB-CH0 medium in each roller bottle. The cells were then incubated at 37° C. for 3 days, at which time the media/beads were removed. rBPI-IgG fusion products were purified from the beads as described below. Second and third production cycles (2 days/cycle) with the recovered cells in fresh HB-CHO media containing Sepharose beads may also be performed in order to increase the yield of rBPI-IgG from each roller bottle. Similar procedures may be used with T-flasks instead of roller bottles.

B. Isolation of rBPI-IgG Fusions

Growth media and S-Sepharose resin were removed from roller bottles, pooled and left undisturbed for at least 15 minutes to allow the S-Sepharose to settle to the bottom of the container. The bulk of the media, clear of resin, was removed by decanting and filtered through a device, such as a fritted disc, allowing removal of cells and retention of the S-Sepharose. Following the decanting of the media, the S-Sepharose was suspended in an acetate buffer comprising 20 mM sodium acetate/acetic acid at pH 4.0 containing 0.1M NaCl, stirred gently, and allowed to settle for 10 minutes. The buffer was then decanted and the S-Sepharose was transferred in a small volume to an appropriately sized liquid chromatography column. An Econocolumn (BioRad, Richmond, Calif.), 2.5×10 cm was used for a 20 to 40 gram pooled sample of S-Sepharose resin collected from 3 to 5 roller bottles. The packed S-Sepharose column was washed with 0.1M NaCl-Acetate buffer until the A280 absorbance of the eluate was equal to that of the 0.1M NaCl-Acetate buffer. The column was washed sequentially with 0.7M NaCl-Acetate buffer, with 1.0M NaCl-Acetate buffer and with 1.5M NaCl-Acetate buffer. Fractions were collected. The rBPI-IgG fusion protein eludes predominantly in the 1.5M NaCl-Acetate buffer fraction.

EXAMPLE 4

A. Generation of Polyclonal Antisera Against rBPI (1–199)

For the purpose of exemplification, the procedures used in this example were performed on the BPI-Ig fusion protein expressed from cells which were transfected with pING4512 DNA. Polyclonal antisera were generated in rabbits (Cocalico Biologicals, Reamstown, Pa.) using a purified rBPI(1–199) fragment as the antigen. The rabbit antisera were found to be cross reactive with the eliciting antigen as well as with recombinant BPI holoprotein ("rBPI-50") and with an rBPI-IgG fusion protein (the expression product of pING4512), although the immunoreactivity was greater toward the eliciting antigen than toward either holo rBPI or the fusion. The antibodies were effective for use in EL1SA, on Western Blots, and for immunoprecipitation and were used at greater than a 1:2000 dilution for most applications.

B. Procedures for SDS-Polyacrylamide Gel Electrophoresis and Western Blot

The protein samples from the 1.5M NaCl-acetate buffer eluate of the S-Sepharose column (described in Example 2) which contained the fusion protein secreted from pING4512 were separated by SDS-Polyacrylamide Gel Electrophoresis (SDS-PAGE) under reducing conditions. The samples were first adjusted to contain less than 0.5 ml NaCl and were then precipitated by the addition of ice-cold acetone to a final concentration of 75% acetone. The resulting protein precipitate was then pelleted by centrifugation at greater than 10,000 rpm for 5 to 10 minutes. The supernatant was removed and the precipitate was suspended in a gel sample buffer containing 8M Urea, 2% SDS, 60 mM Tris HCl at pH 6.8 with or without 50 mM dithiothreitol. The suspended samples and appropriate protein molecular weight standards (BioRad, Richmond, Calif. and BRL, Bethesda, Md.) were heated separately to 95° C. for 3–5 minutes and then loaded onto uniform percentage or gradient percentage polyacrylamide gels (BioRad) and separated using a mini Protean II gel electrophoresis apparatus (BioRad). Following electrophoresis the gels were used directly for Coomassie staining (0.5% Coomassie Brilliant Blue-R, 25% isopropanol, 10% acetic acid, stained for 1 hour, destained with 10% methanol, 10% acetic acid) or were used for electrotransfer. The proteins separated by SDS-PAGE were electrotransferred along with appropriate prestain standards proteins (BioRad) onto either nitrocellulose (BA85, Schleicher and Schuell, Keene, N.H.) or PVDF (Immobilon-P, Millipore, Bedford, Mass.) membranes. The transfer was achieved in 10% CAPS (cyclohexylamino-1-propane sulfonic acid), 10% methanol, pH 11.5 for 20 minutes at 0.5 amps. The resulting blots were used for amino acid sequencing or were processed either with Protein-A-gold to detect IgG heavy chain or with a 1:2000 dilution of rabbit anti-rBPI antibody followed by 1–1000 dilution of peroxidase conjugated goat anti rabbit antibody to detect rBPI. For the rBPI Western blot, the Western Lite Chemiluminescent Detection System (Tropix System, Bedford, Mass.) was used according to the manufacturer's instructions to develop the blots. Gelatin (BioRad) at 0.25% was used in place of Tropix I-Block and the membranes were not dried following electrotransfer. The processed membranes were exposed to Cronex 4 film (Dupont, Wilmington, Del.).

FIG. 1 demonstrates the results of SDS-polyacrylamide gel electrophoresis of the BPI-Ig fusion protein produced from pING4512. The left lane is Coomassie stained gel. The middle and right lanes were electrotransferred to PVDF membranes and treated as for Western blots. The middle lane is a blot developed using Protein-A-Gold to detect human IgG. The right lane is a blot developed using rabbit anti-BPI antibody followed by peroxidase conjugated goat anti-rabbit with detection using the Western Lite Chemiluminescent Detection Kit as described in Example 4.

C. Molecular Weight Determination

Samples eluted from S-Sepharose with 1.5m NaCl-acetate buffer were analyzed using SDS-PAGE followed by Coomassie staining according to Section B above revealing, as the major component, a protein with an apparent molecular weight of 95,000 to 110,000 daltons corresponding to the size expected for a homodimer of the rBPI-IgG fusion. Under reducing conditions, the 100 kd protein has an apparent molecular weight of 45,000 to 50,000 daltons, corresponding to the size expected for a monomer of the same fusion.

D. Amino Terminal Amino Acid Sequence

The 1.5M NaCl-Acetate buffer eluate of the S-Sepharose column described in Example 2 above was run on a 12% SDS-polyacrylamide gel, transferred to PVDF membranes, and Coomassie stained to visualize the 100 kd protein band which was then sliced from the membrane and subjected to amino terminal amino acid sequencing using a gas phase sequenator (Applied Biosystems, Model 470A). The amino terminal amino acid sequence of the 100 kd protein was determined to be Val-Asn-Pro-Gly-Val-Val (SEQ. I.D. NO. 19). That sequence corresponds to the expected amino terminal sequence arising from in vivo secretory pathway cleavage of the signal sequence between amino acids −1 and +1 of the signal sequence.

E. Evidence for the Hybrid Nature of the Fusions

Samples of the same 1.5M NaCl-Acetate buffer eluate, run on SDS polyacrylamide gels, were electrotransferred to PVDF membranes and prepared for Western blot. Western analysis was performed using Protein-A-Gold to directly detect the IgG heavy chain portion of the fusion protein. The results demonstrated that the 100 kd band contained IgG protein sequences. Western analysis was performed on an identical electrotransferred sample processed using rabbit anti-BPI(1–199) antibody to detect the BPI portion of the rBPI-IgG fusion protein. This Western analysis demonstrated the presence of BPI-immunoreactive protein in the 95 kd to 110 kd region with only minor amounts of BPI-specific immunoreactivity at less than 95 kd and greater than 110 kd. Western blot analysis of the rBPI-IgG fusion protein produced from plasmid pING4512 is shown in FIG. 1, wherein the left lane is Coomassie stained, the middle lane was developed with Protein-A-Gold and the right lane was developed using the rabbit antibody.

F. Activity Assays

Clinically relevant activities of BPI are presented by the fragment corresponding to the amino terminal region of BPI. These activities include the permeability increasing and bactericidal activities in Gram negative cells, Elsbach, et al. *J. Biol. Chem.*, 262:14891 (1987), as well as its ability to bind soluble lipopolysaccharide (LPS) and to neutralize activation of neutrophils. The retention of these activities by the rBPI-IgG fusion proteins would suggest that the BPI portion of the fusion is in a correctly folded conformation. The CH2-CH3 (Fc) portion of the fusion should display Fc receptor- and complement-binding activities. The retention of these activities would demonstrate that the Fc region of the fusion is also in a correctly folded conformation. Several assays were performed to assess the BPI- and Fc-associated activities of the various fusion proteins purified from CHO cells.

1. Lipopolysaccharide-Western Assay

Figure 2:
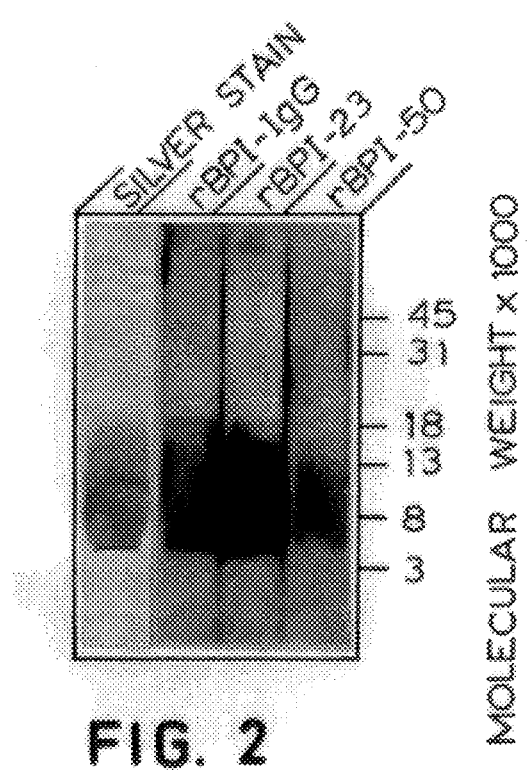
FIGS. 2 and 3 depict the binding of soluble, recombinant-produced BPI ("rBPI") and rBPI-Ig to LPS.
Figure 3:
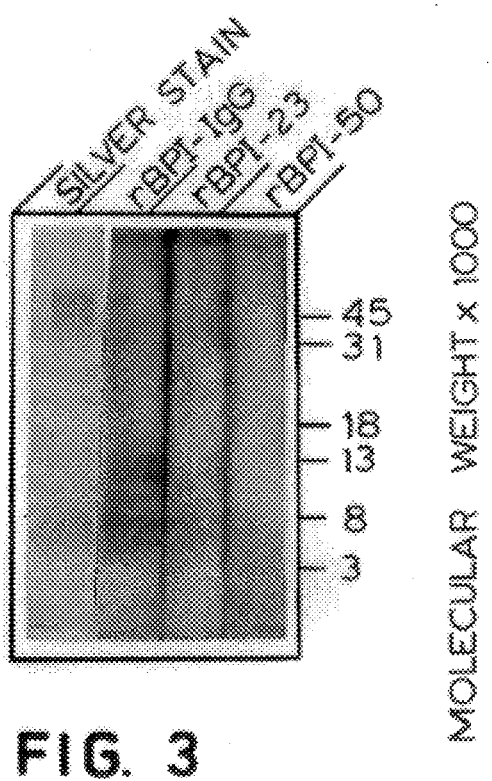

Samples, ranging in size from 20 µg to 60 µg each, of *E. coli* (Strain 0111-B4) or *S. minnesota* (Rd mutant) lipopolysaccharide (LPS, Sigma, St. Louis, Mo.) were size fractionated by gel electrophoresis using 15% SDS-polyacrylamide gels as described above for the protein SDS-PAGE. Following electrophoresis, the LPS samples were electrotransferred from the polyacrylamide gel to nitrocellulose (BA 85, Schleicher and Schuell) together with prestained protein standards (BioRad) using CAPS buffer as described above for the electrotransfer of protein. These LPS blots were processed by soaking the membrane in 30 mg/ml BSA, 50 mM Tris, 0.2M NaCl, pH 7.4 (TBS) for 30 min at 37° C. and then incubating the membrane in a solution containing 2–4 µg of partially purified rBPI-IgG fusion protein or a control recombinant protein [rBPI(1–199) or holo-rBPI] in TBS for 12 to 18 hours at 21° to 24° C. The membranes were then washed with TBS, changing the solution at least 3 times over a period of 30 minutes. The membranes were then incubated for 3 hours in a 1:1000 dilution of rabbit anti-rBPI(1–199) antibody in TBS, 1 mg/ml BSA solution. After washing at least 3 times, the membranes were processed using the Western Lite Chemiluminescent Detection System as described above in Section B. A duplicate lane of the LPS gel was silver stained and the results for Rd. *S. minnesota* and 0111-B4 binding are respectively set out in FIGS. 2 and 3. The far left lane in each gel is the silver strained LPS. As shown by the Figures, rBPI-IgG fusion protein produced from plasmid pING4512 binds LPS fixed to the nitrocellulose as well or better than the control recombinant proteins, rBPI(1–199) and holo-rBPI.

2. Lipopolysaccharide Capture Assay rBPI-IgG samples and recombinant BPI proteins [rBPI (1–199 and holo rBPI] at several dilutions in a final volume of 50 µl were bound to 96 well Immulon-2 flat bottom multiwell plates (Dynetech Labs) in the presence of PBS. Following binding, the plates were washed with 0.05% Tween-20 and PBS and were incubated with *E. coli* 0111-B4 or *S. minnesota* Rd lipopolysaccharide (20 pg) in 0.05% Tween-20 and PBS for 2 hours at 37° C. The plate was then washed vigorously with 0.05% Tween-20, PBS, developed using the Limulus Amebocyte Lysate kit (Whittaker, Walkersville, Md.) and read at 405 nm in an EL309 microplate autoreader (Bioteck Instruments, Winooski, Vt.). The results are graphically set out in FIG. 4 which shows that immobilized rBPI-IgG binds soluble LPS as well or better than the control recombinant proteins, rBPI(1–199) or holo-rBPI.

Figure 4:
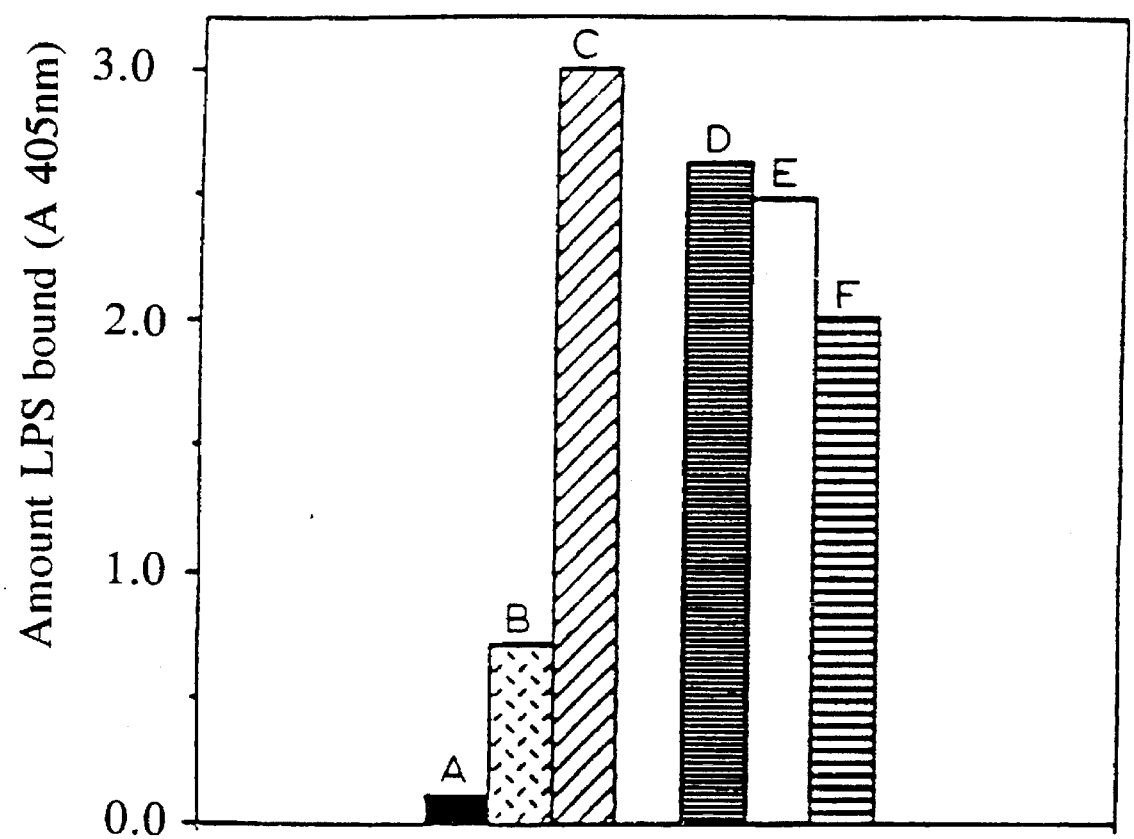
FIG. 4 depicts the binding of immobilized rBPI-Ig to soluble LPS.

Specifically, FIG. 4 depicts results of the LPS capture assay wherein the sample contained No LPS (column A), no BPI (column B), LPS alone (column C), the rBPI-Ig fusion protein produced from pING4512 (column D), rBPI(1–199) (column E), or holo-rBPI (column F).

3. E. coli Growth Assays

Bactericidal activity of BPI can be measured in several ways. In all such assays, the bactericidal effect of BPI can be reduced or eliminated by the addition of about 100 mM magnesium chloride. One such assay, the broth growth inhibition assay was applied to the rBPI-IgG fusions according to the invention.

Figure 5:
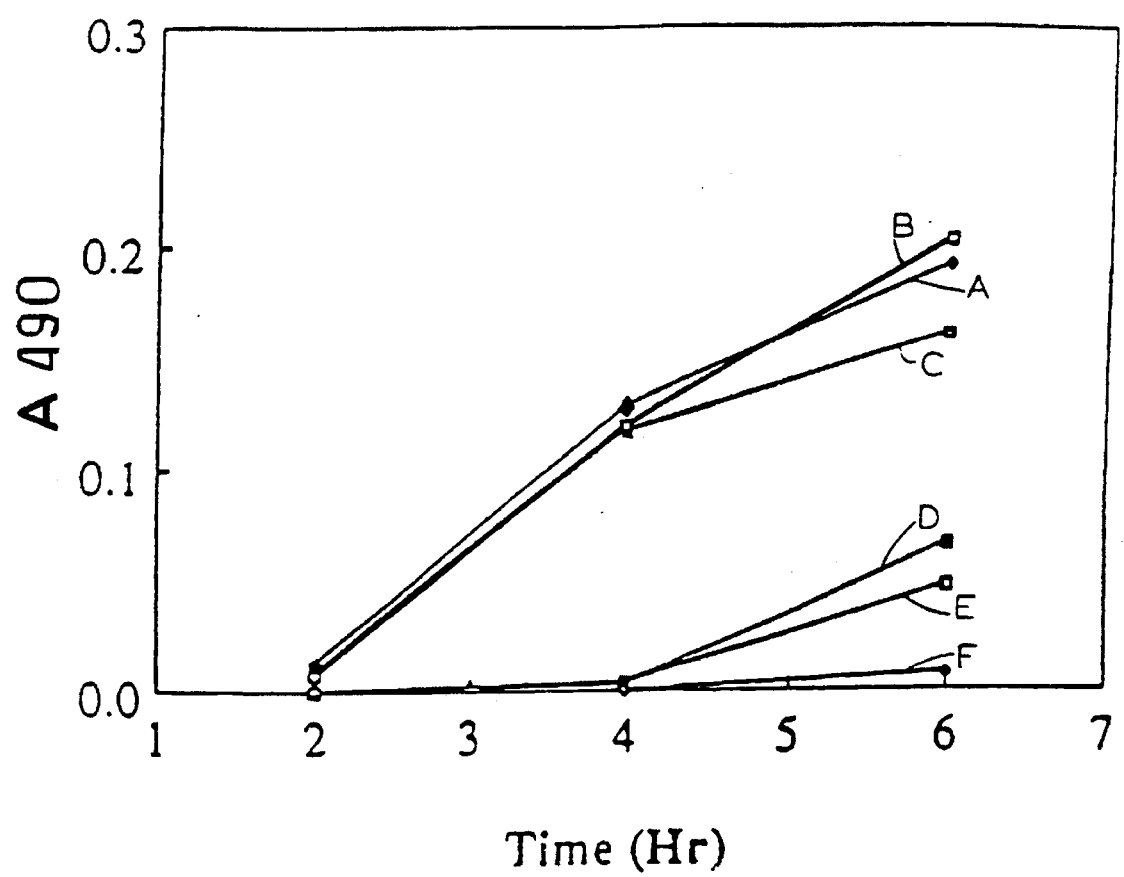
FIG. 5 depicts the bactericidal activity of products of the invention on *E. coli* J5 cells.

This assay is based on the inhibition of broth growth following treatment of E. coli with BPI fragments or rBPI-IgG fusions proteins. Cells used in this assay were J5 cells (a "rough" strain of E. coli with short-chain LPS) which were grown in a triethanolamine-buffered mineral salts medium (Simon, et al., Proc. Nat'l Acad. Sci. (USA), 51:877 (1964)) which renders the cells especially sensitive to the actions of BPI. The cells were washed and resuspended in 0.9% NaCl to a density of about $5 \times 10^8$/ml. Approximately $5 \times 10^6$ to $1 \times 10^7$ cells were then incubated for 30 minutes with the pING4512 and pING4514 rBPI-Ig fusions proteins or recombinant protein, rBPI(1–199) at 5 µg/ml of a buffered solution (10% Hanks Balanced salts, 40 mM Tris-HCl, pH 7.5, 0.1% casamino acids) in a total volume of 200–400 µl. The fusion protein were also incubated with E. coli in the presence of 100 mM $MgCl_2$. Following incubation with the rBPI-IgG fusion proteins or the rBPI(1–199) fragment alone, the cells were diluted with 10 volumes of nutrient broth supplemented with 0.9% NaCl and growth was followed for several hours. The results, as shown in FIG. 5, demonstrated that the fusion proteins substantially retained the bactericidal activity associated with the rBPI(1–199) protein, wherein line A represents treatment with the fusion protein produced by pING4512 and magnesium; line B represents treatment with the fusion protein produced by pING4514 and magnesium; line C represents the control [buffer only]; line D represents treatment with the fusion protein produced by pING4514; line E represent treatment with the fusion protein produced by pING4512; and line F represents treatment with BPI(1–199). As expected, this activity was inhibited by magnesium chloride. Similar results are obtained with the pING4515 rBPI-IG fusion protein.

4. Fc Receptor Binding Assay

The binding of the rBPI-Ig fusion proteins to Fc receptors was examined using the human monocytic cell line, U937, which is known to express both the high affinity FcR1 (CD64) receptor ($Kd=10^{-8}$ to $10^{-9}$) and the lower affinity FcRII (CD32) receptor ($Kd=10^{-7}$ or higher).

For this assay, U937 cells were incubated at 4° C. in DMEM+1% BSA, for 3 hours in V-bottom 96-well plates ($3 \times 10^5$ cells/well, 100 µl) with either of two rBPI-Ig fusion proteins (derived from pING4512 and pING4514) at concentrations from 100 nM to 0.8 nM or with a chimeric mouse-human antibody positive control at concentrations from 67 to 0.5 nM. The cells were next washed 3 times with DMEM +1% BSA (200 µl/wash; centrifuge plates at 1000 RPM, 4° C.). Goat α-gamma peroxidase (1/4000 dilution) or α-kappa peroxidase (1/1000 dilution) was added to the wells and the cells were incubated at room temperature for 1 hr. Following 3 washes, as described above, 100 µl color development reagent (5 mg ortho phenylenediamine dihydrochloride [o-PD] in 12.5 ml citrate buffer +5 µl $H_2O_2$) was added to each well and the plates were incubated for 15–20 min. at room temp. The color development was stopped by addition of 100 µl/well of 1.8M $H_2SO_4$ and absorbance at A490 was determined.

Figure 6:
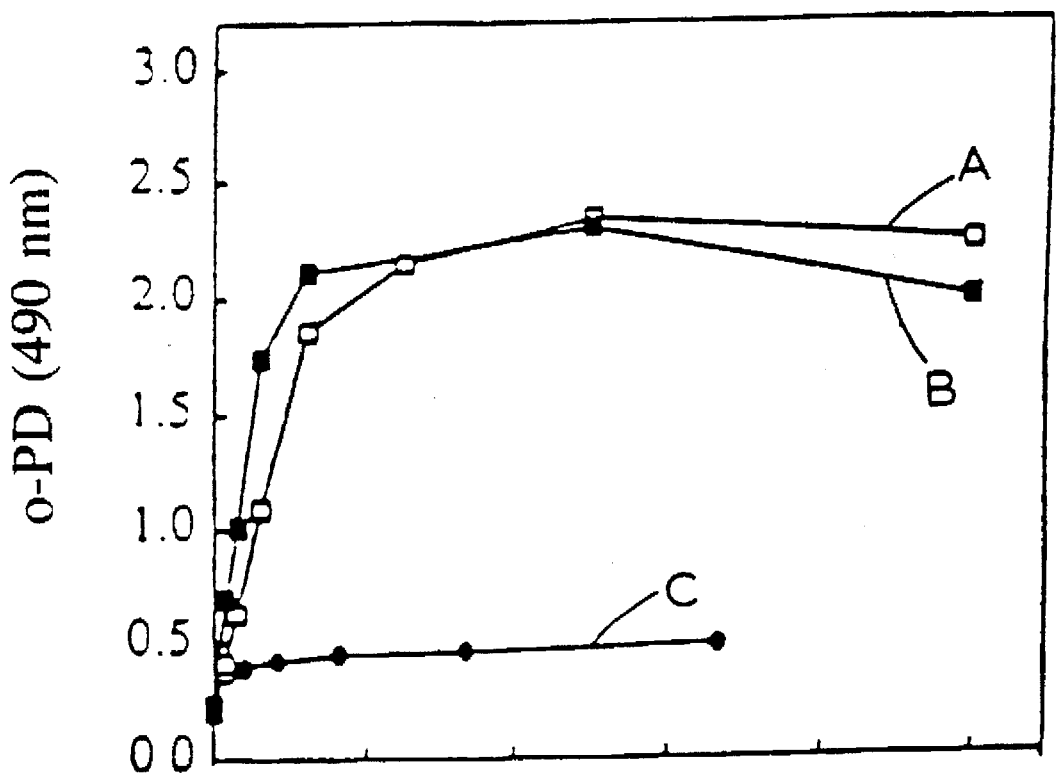
FIGS. 6 and 7 depict the binding of products of the invention to U937 cells as detected with goat anti-human gamma peroxidase.
Figure 7:
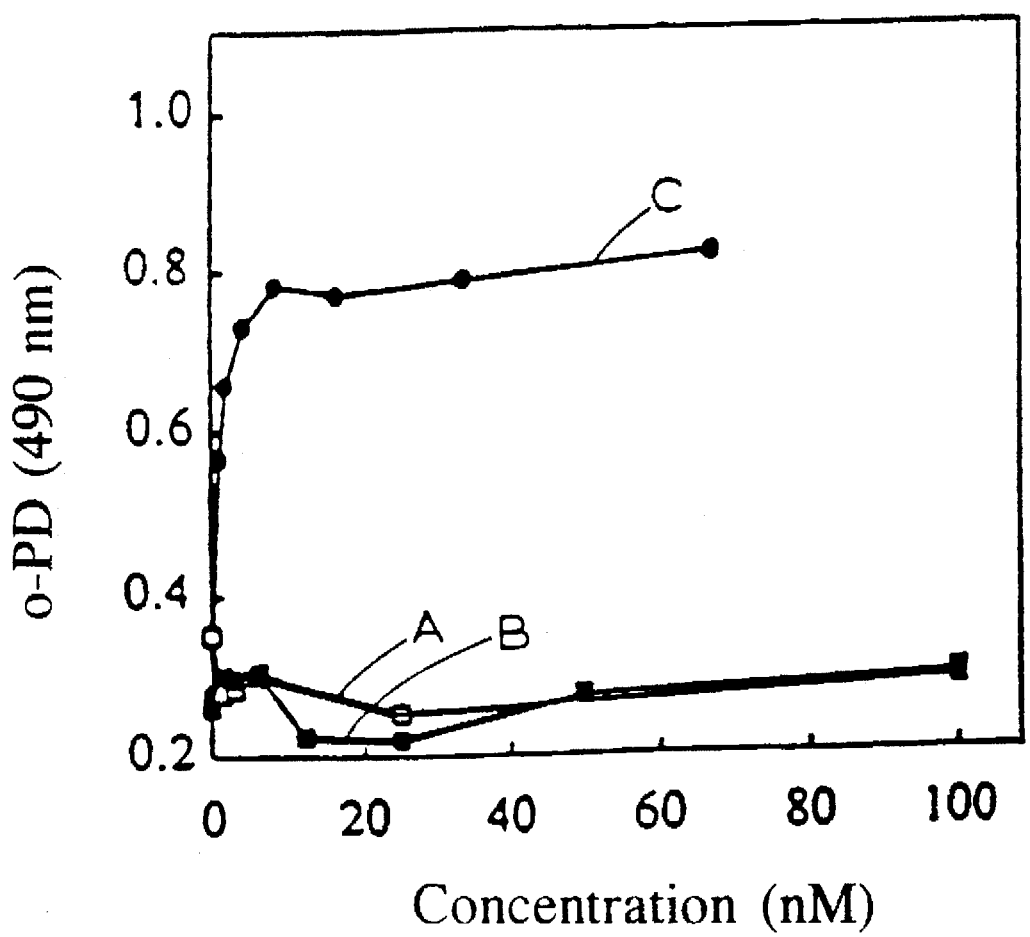
Figure 8:
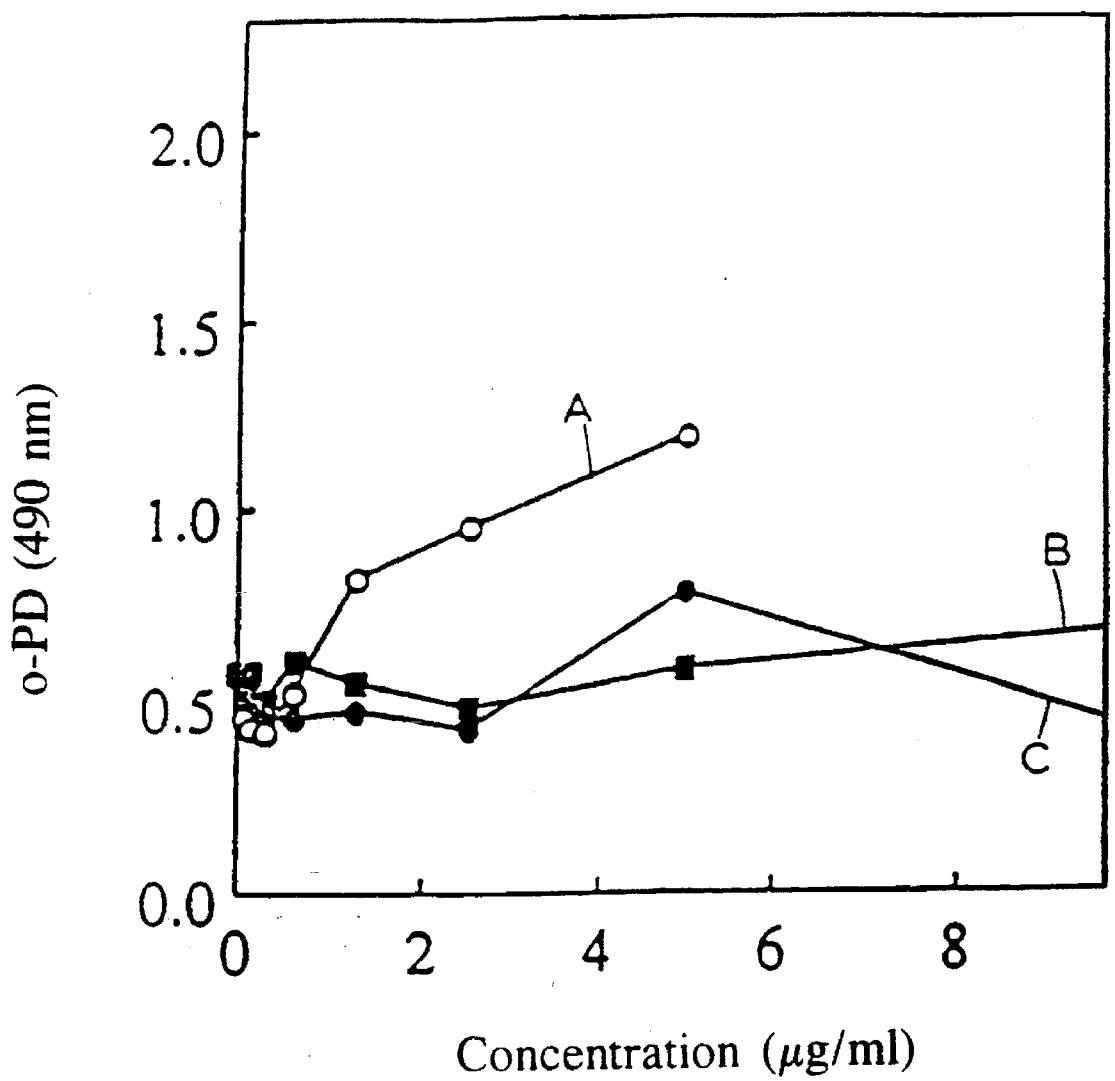
FIG. 8 depicts the differential binding of products of the invention to the surface of U937 cells.

The results for detection with the α-gamma and α-kappa antibodies, shown respectively in FIGS. 6 and 7, demonstrate that the rBPI-Ig fusion proteins as well as the chimeric H65 IgG control bound to the U937 cells. In FIGS. 6 and 7, line C represents the chimeric H65 IgG control; line B represents the BPI-Ig fusion protein produced by pING4514; and line A represents the BPI-Ig fusion protein produced by pING4512. The relative affinities of these proteins for the U937 cells were estimated as follows: pING4512 product= ~7 nM; pING4514 product=~4 nM; and chimeric H65 IgG=~0.2 nM. These results suggest that the high affinity receptor (FcRI) is being bound by both the rBPI-Ig fusions and the chimeric H65 IgG. However, binding to other receptors (possibly the lower affinity FcRII) by the rBPI-IgG fusions cannot be ruled out since the absorbance for these fusions at saturation was significantly higher (A490=2.0) than that of the chimeric IgG at saturation (A490=0.4). These results may suggest that the fusions either bound to a greater number of receptors than the chimeric IgG or that the detection of the bound fusions with the α-gamma antibody was more efficient than detection of the bound chimeric IgG. Several other chimeric IgG's were tested (in comparison to the pING4512 fusion) with U937 cells and these behaved in a similar fashion to chimeric H65 IgG. A similar experiment as that described above was performed with the U937 cells and the pING4512 fusion expression product, chimeric H65 and rBPI(1–199), but using rabbitα-human-BPI antiserum to detect the bound rBPI-Ig on the surface of the cells. The results, shown in FIG. 8, (wherein line A represents the BPI-Ig fusion protein produced by pING4512; line B represents rBPI(1–199); and line C represents the chimeric H65 IgG Control) demonstrate that only the rBPI-Ig fusion protein could be detected on the surface of the U937 cells.

EXAMPLE 5

Properties of rBPI-Ig Fusion Proteins

The ability of rBPI-Ig fusion proteins of the invention to bind heparin, the pharmacokinetic properties of the fusions, In vivo activity, and LAL inhibition were next measured.

A. Comparative Heparin Binding of rBPI-Ig and rBPI(1–199)

A direct $^3$H-heparin binding assay was utilized to analyze the comparative binding of rBPI(1–199) and rBPI-Ig fusions to heparin. The assay was based on the ability of a derivatized nylon membrane to bind proteins with high capacity. Such a membrane has been incorporated into the bottom of 96-well microtiter plates by Millipore Corp. (Bedford Mass.) (Multiscreen IP plates) and may be punched out of each well for scintillation counting.

To conduct the assay, rBPI(1–199) or an rBPI(1–191)-IgG fusion protein was added to the wells of a 96-well plate at a concentration of 100 pmol/well diluted with phosphate buffered saline (PBS), pH 7.4 nylon membrane. Upon absorption to the membrane, the wells were blocked with a blocking buffer comprising 0.1% bovine serum albumin (BSA) in PBS. Serial dilutions of $^3$H heparin (DuPont, NEN, Wilmington, Del.) were made from 4–5 µg/ml in the blocking buffer and incubated in the wells coated with either rBPI(1–199) and rBPI(1–191)-IgG for one hour at 4° C. After one hour, unbound heparin was aspirated and the wells were washed three times with blocking buffer, dried, and removed for quantitation of bound $^3$H-heparin by liquid scintillation counting.

Figure 9:
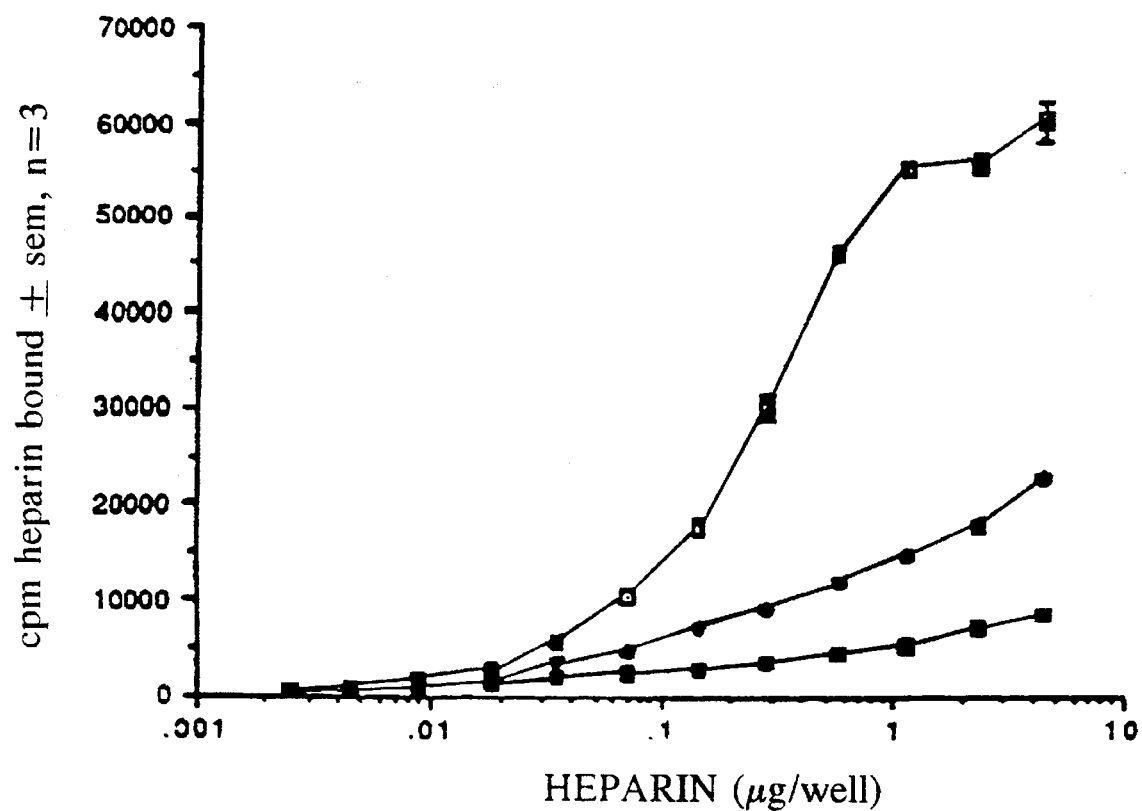
FIG. 9 depicts binding of rBPI(1–199)-Ig fusion protein and rBPI(1–199) to $^3$H heparin.

Results of the assay are shown in FIG. 9, wherein open squares represent binding rBPI(1–199) to heparin; diamonds represent binding of rBPI(1–191)-Ig fusion proteins to heparin; and closed squares represent background. The results in FIG. 9 indicate that, while rBPI(1–199) binds heparin within the expected range of BPI $K_d$ values (apparent affinity=114 ±30 nM), the fusion did not exhibit similar binding characteristics. Fusion proteins did not reach saturation even at the highest $^3$H heparin concentration tested (2.5 µM). Thus, rBPI(1–191)-IgG fusion binds heparin approximately three times higher than background, but not as well as rBPI (1–199).

B. Pharmacokinetic Properties of rBPI-Ig Fusion Proteins

The in vivo pharmacokinetic properties of rBPI-Ig fusion were determined by administering an intravenous injection of 1 mg/kg $^{125}$I-BPI(1–191)-IgG fusion protein or buffer to male CD rats. Blood samples were then collected from 0.5 minutes until 24 hours after administration of the fusion protein or buffer and measured for $^{125}$I radioactivity. The serum samples were also analyzed by TCA precipitation and by SDS-PAGE to determine the amount of serum radioactivity associated with rBPI-Ig and higher molecular weight proteins.

Table 2 below and FIG. 10, wherein triangles represent rBPI-Ig fusions and circles represent rBPI(1–199), provide pharmacokinetic parameters obtained from the foregoing study. The Table provides quantitative of the data taken from the curves on FIG. 10. As noted in both Table 2 and FIG. 10, serum concentrations of fusion protein followed a biphasic clearance for up to two hours post-dosing, with an αt1/2 of 2.5 ±0.2 minutes and a β-t1/2 of 39 ±13 minutes. The mean residence time (MRT) (a measure of the persistence of the fusion protein in the body), clearance, central volume distribution (Vc), and steady state Volume distribution (Vss) are also shown in Table 2. Also in that table are data representing the area under the curves in FIG. 10 which provides an additional measure of persistence in the body. There is no statistically-significant difference in any pharmacokinetic property measured in Table 2 or FIG. 10 between rBPI(1–199) and rBPI(1–191)IgG fusion protein.

TABLE 2

Figure 10:
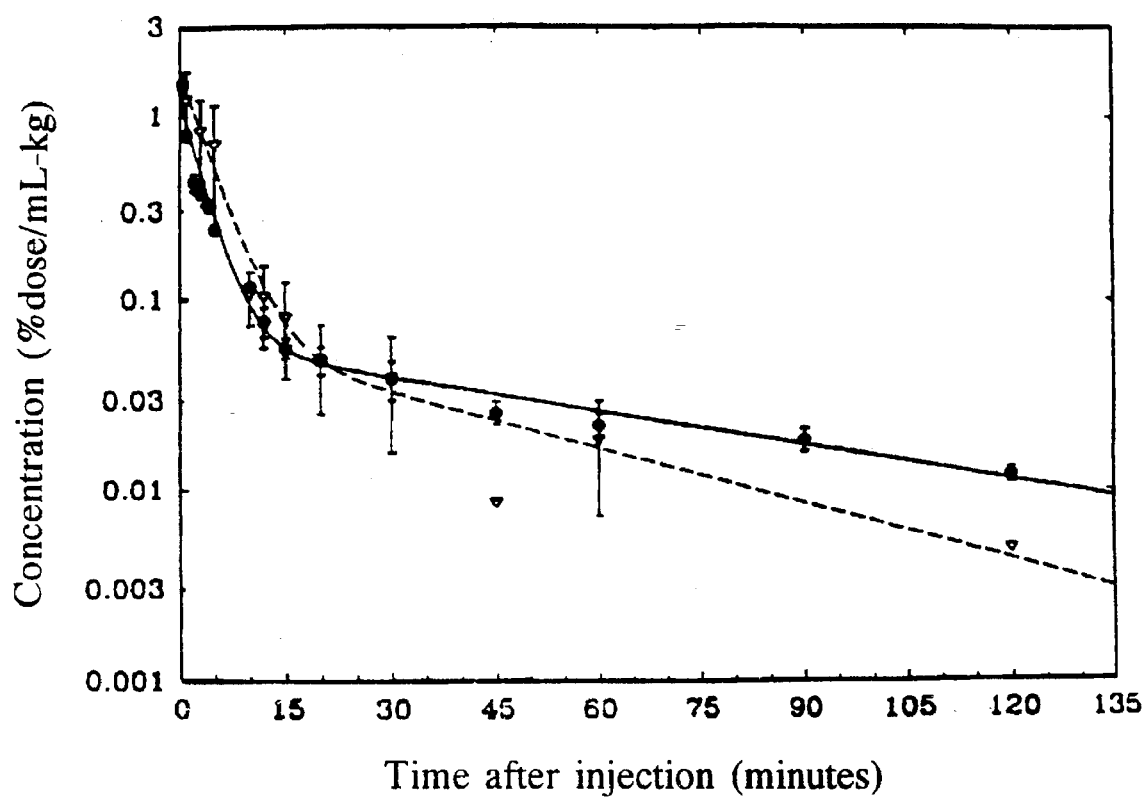
FIG. 10 depicts the serum clearance of $^{125}$I rBPI(1–199)-Ig fusion proteins and $^{125}$I rBPI(1–199) in rats.

Pharmacokinetic Parameter Values From Serum Clearance Curves In FIG. 10 For 1 mg/kg $^{125}$I rBPI (1–199) And $^{125}$I rBPI(1–199) Fusion Protein

| BPI Form | Area Under Curve % Dose/ mL-kg | $V_c$ mL/kg | $V_{ss}$ mL/kg | Clearance ml/min/kg | MRT minutes | αt 1/2 minutes | βt 1/2 minutes |
|---|---|---|---|---|---|---|---|
| rBPI(1–199) n = 60 | 8.31 ± 0.36 | 71.8 ± 7.8 | 467 ± 47 | 12.0 ± 0.5 | 38.8 ± 4.2 | 1.87 ± 0.19 | 45.7 ± 4.8 |
| rBPI(1–191)-IgG Fusion n = 2 | 6.96 ± 2.14 | 100.4 ± 18.1 | 420 ± 157 | 15.9 ± 4.9 | 25.9 ± 1.9 | 2.53 ± 0.16 | 39.1 ± 12.9 |

C. In vivo Efficacy of rBPI-Ig Fusion Proteins

A study was conducted to evaluate the efficacy of rBPI-IgG fusions in an in vivo lethal endotoxemia animal model. In this study, male ICR mice were administered an intravenous injection of a mixture of actinomycin-D (800 µg/kg) and either 0.1 µg/kg or 0.3 µg/kg of endotoxin (*E. coli* 0111:B4). Immediately following injection of actinomycin-D and endotoxin, the mice were administered a second intravenous injection of either rBPI-IgG fusion protein or a BPI formulation buffer comprising 20 mM sodium citrate, 150 mM sodium chloride with 0.1% poloxamer and 0.002% polysorbate 80, pH 5.0 (the "buffer control" group in Table 3). A group was given a second injection of PBS (phosphate buffered saline) (the "negative control" group in Table 3) Deaths were then recorded daily for a period of seven days. The results of this study are presented below in Table 3.

TABLE 3

| LPS Dose μg/Kg | Actinomycin-D Dose μg/Kg | rBPI-IgG Dose mg/Kg | Deaths/Total Animals | % Mortality |
|---|---|---|---|---|
| 0 | 800 | Negative control | 0/15 | 0 |
| 0.1 | 800 | Buffer control | 12/15 | 80 |
| 0.1 | 800 | 0.5 | 11/15 | 73 |
| 0.1 | 800 | 5.0 | 7/15 | 47 |
| 0.3 | 800 | Buffer control | 15/15 | 100 |
| 0.3 | 800 | 0.5 | 14/15 | 93 |
| 0.3 | 800 | 5.0 | 9/15 | 60* |

*-Statistically significant difference compared to buffer ($P \leq 0.05$) as measured by Chi square.

The results of this study indicate that rBPI-IgG fusion proteins p at 5 μg/kg rovide significant protection from the lethal effects of endotoxin in actinomycin-D sensitized mice at endotoxic challenge of 0.3 μg/kg.

D. LAL Inhibition Assay rBPI(1–199) and rBPI(1–191)-Ig fusions were subjected to a Limulus Lysate (LAL) inhibition assay to determine the LPS binding properties of those compounds. Specifically, rBPI(1–199) or rBPI(1–191)-Ig fusion were mixed in Eppendorf tubes with a fixed concentration of *E. coli* O113 LPS (4 ng/ml final concentration) and incubated at 37° C. for 3 hours with occasional shaking. Following incubation, 360 μl D-PBS was added per tube to obtain an LPS concentration of 200 pg/mL for the LAL assay. Each sample was then transferred into Immulon II strips (Dynatech, Chantilly, Va.) in volumes of 50 μl per well.

Limulus Lysate (Quantitative chromogenic LAL kit, Whitaker Bioproducts, Inc., Walkersville, Md.) was added at 50 μl per well and the wells were incubated at room temperature for 25 minutes. Chromogenic substrate was then added at a volume of 100 μl per well and was well mixed. After incubation for 20 to 30 minutes at room temperature, the reaction was stopped with addition of 100 μl of 25% acetic acid. Optical density at 405 nm was then measured in a multiplate reader (Vmax, Medical Devices Menlo Park, Calif.).

Figure 11:
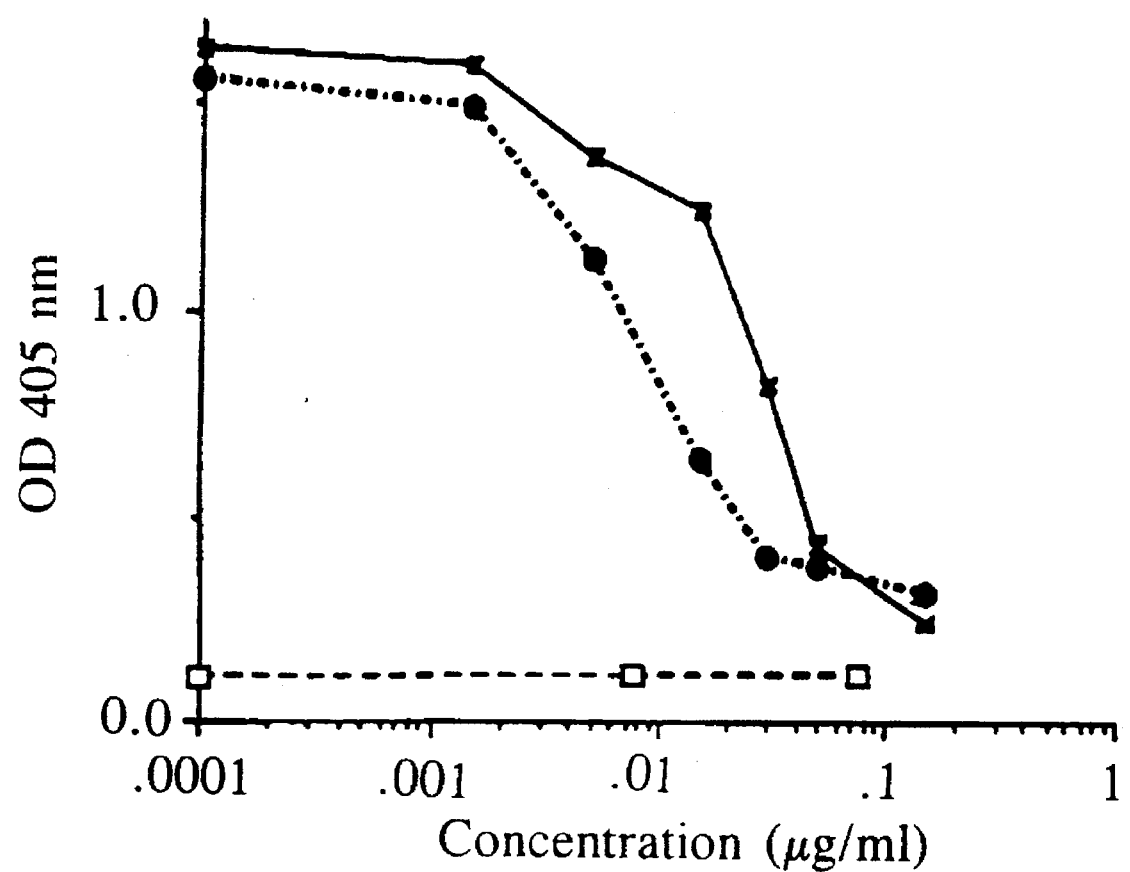
FIG. 11 depicts the results of an LAL inhibition assay involving rBPI (1–199) and rBPI(1–199)-Ig fusion proteins.

Results of the LAL assay are shown in FIG. 11, wherein the solid line represents results obtained with rBPI(1–191)-Ig fusions, the dotted line containing filled circles represents results obtained with rBPI(1–199) proteins, and the dotted line containing open squares represents a non-LPS control. As indicated in the Figure, there is no significant difference in assay results between rBPI(1–199) and rBPI(1–191)-Ig fusion proteins in terms of their ability to inhibit LPS stimulation in the Limulus amoebocyte lysate assay.

Numerous modifications and variations in the practice of the invention are expected to occur to those skilled in the art upon consideration of the foregoing description of the presently preferred embodiments thereof. Consequently, the only limitations which should be placed upon the scope of the present invention are those which appear in the appended claims.

We claim:

1. A hybrid fusion protein comprising, at its amino terminal, a bactericidal/permeability-increasing protein or a biologically active fragment thereof and, at its carboxy terminal, at least one constant domain of an immunoglobulin heavy chain or an allelic variant thereof.

2. The hybrid fusion protein according to claim 1 comprising two immunoglobulin heavy constant region domains.

3. The hybrid fusion protein according to claim 2 wherein said two heavy chain constant regions are the CH2 and CH3 domains.

4. The hybrid fusion proteins according to claim 1 further including an immunoglobulin hinge region in a position between the bactericidal/permeability-increasing protein and immunoglobulin portions of the fusion.

5. The hybrid fusion protein according to claim 1 consisting essentially of the initial 191 amino acid amino terminal residues of bactericidal/permeability-increasing protein.

6. The hybrid fusion protein according to claim 1 consisiting essentially of the initial 199 amino acid amino terminal residues of bactericidal/permeability-increasing protein.

7. The hybrid fusion protein according to claim 1 consisiting essentially of the initial 176 amino acid amino terminal residues of bactericidal/permeability-increasing protein.

8. The hybrid fusion protein according to claim 1 wherein a cysteine residue at position 132 in said bactericidal/permeability-increasing protein is replaced with another amino acid.

9. The hybrid fusion protein according to claim 8 wherein said cysteine residue at position 132 in said bactericidal/permeability-increasing protein is replaced with alanine.

10. The hybrid fusion protein according to claims 1, 2, 3, 4, 5, 6, 7, 8, or 9 comprising human protein sequences.

11. The hybrid fusion protein according to claim 1 in homodimeric form.

12. The hybrid fusion protein according to claim 1 wherein said constant domain of an immunoglobulin heavy chain is selected from the group consisting of IgG, IgA, and IgM immunoglobulins.

13. A DNA sequence encoding a hybrid fusion protein comprising, at its amino terminal, a bactericidal/permeability-increasing protein or a biologically active fragment thereof and, at its carboxy terminal, at least one constant domain of an immunoglobulin heavy chain or an allelic variant thereof.

14. The DNA sequence according to claim 13 comprising a DNA sequence encoding two immunoglobulin heavy chain constant region domains.

15. The DNA sequence according to claim 14 comprising a DNA sequence encoding the CH2 and CH3 heavy chain constant region domains.

16. The DNA according to claim 13 comprising a region encoding from the initial 176 amino terminal residues of BPI to the initial 199 amino terminal residues of bactericidal/permeability-increasing protein.

17. The DNA according to claim 13 comprising a region encoding the initial 191 amino terminal residues of bactericidal/permeability-increasing protein.

18. The DNA according to claim 13 comprising a region encoding the initial 199 amino terminal residues of bactericidal/permeability-increasing protein.

19. A DNA vector comprising a DNA sequence according to claim 13.

20. The DNA vector according to claim 19 selected from the group consisting of pING4512 (ATCC 75239), pING4514 (ATCC 75240), pING4515 (ATCC 75241), and pING4517 (ATCC 75242).

21. A host cell stably transformed or transfected with a DNA sequence according to claim 13 in a manner allowing expression in said host cell of the hybrid fusion protein encoded thereby.

22. A procaryotic host cell according to claim 21.

23. A eucaryotic host cell according to claim 21.

24. A host cell according to claim 21 having the accession number ATCC CRL 11042.

25. A host cell according to claim 21 having the accession number ATCC CRL 11043.

26. A host cell according to claim 21 having the accession number ATCC CRL 11044.

27. A method for producing a hybrid fusion protein comprising, at its amino terminal, a bactericidal/permeability-increasing protein or a biologically active fragment thereof and, at its carboxy terminal, at least one constant domain of an immunoglobulin heavy chain or an allelic variant thereof, said method comprising growing host cells according to claim 21 in a suitable culture medium; and isolating said hybrid fusion protein from said host cells or said culture medium.

28. A pharmaceutical composition comprising the hybrid fusion protein according to claim 1 and a pharmaceutically acceptable diluent, adjuvant or carrier.

\* \* \* \* \*

UNITED STATES PATENT AND TRADEMARK OFFICE
CERTIFICATE OF CORRECTION

PATENT NO. : 5,643,570
DATED : July 1, 1997
INVENTOR(S) : Theofan et al.

It is certified that error appears in the above-identified patent and that said Letters Patent is hereby corrected as shown below:

Col. 1, line 64, "immunoglobulingene" should be --immunoglobulin gene--.

Col. 22, line 63, "PB5" should be --PBS--.

Col. 23, line 16, "rovide" should be --provide--.

Col. 23, line 16, "P" should be deleted.

Signed and Sealed this

Fifth Day of January, 1999

Attest:

Attesting Officer

*Acting Commissioner of Patents and Trademarks*